United States Patent [19]

Robinson et al.

[11] Patent Number: 5,270,343
[45] Date of Patent: Dec. 14, 1993

[54] PENTA-2,4-DIENAMIDES AND USE AS PESTICIDES

[75] Inventors: John E. Robinson; George S. Cockerill, both of Berkhamsted, England

[73] Assignee: Roussel Uclaf, France

[21] Appl. No.: 898,135

[22] Filed: Jun. 15, 1992

[30] Foreign Application Priority Data

Jun. 25, 1991 [GB] United Kingdom ............... 9113624

[51] Int. Cl.$^5$ .................... A01N 37/24; C07C 235/00
[52] U.S. Cl. .................... 514/622; 514/314; 514/357; 514/438; 514/471; 514/521; 514/522; 514/599; 514/603; 514/624; 546/175; 546/300; 546/330; 546/337; 549/65; 549/77; 549/439; 558/414; 558/393; 564/74; 564/89; 564/172; 564/174; 564/175; 564/180; 564/184; 564/185
[58] Field of Search ............... 564/172, 174, 175, 180, 564/184, 185; 514/622, 624

[56] References Cited

U.S. PATENT DOCUMENTS 4,332,959 6/1982 Anatol et al. .................... 564/175 X Primary Examiner—Richard L. Raymond
Attorney, Agent, or Firm—Bierman and Muserlian

[57] ABSTRACT

The present Application discloses pesticidally active compounds of formula (I):

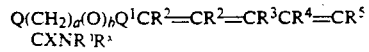

or a salt or propesticide thereof, wherein Q is an optionally substituted aromatic monocyclic or fused bicyclic ring system in which at least one ring is aromatic, or Q is a dihalovinyl group or a group $R^6$—C≡C— where $R^6$ is $C_{1-4}$ alkyl, tri $C_{1-4}$ alkylsilyl, halo or hydrogen; $Q^1$ is a 1,2-cyclopropyl ring optionally substituted by one or more groups selected from $C_{1-3}$ alkyl, halo, $C_{1-3}$ haloalkyl, $C_{2-3}$ alkynyl, or cyano; or is $(CH_2)_7$;

a=0 or 1; b=0 or 1;

$R^2$, $R^3$, $R^4$ and $R^5$ are the same or different with at least one being hydrogen and the others being independently selected from hydrogen, halo, $C_{1-4}$ alkyl or $C_{1-4}$ haloalkyl;

X is oxygen or sulphur;

$R^1$ is phenyl optionally substituted by 1-5 substituents chosen from:
a) $C_{1-4}$ alkyl, $C_{1-4}$ alkoxy, phenoxy and methylenedioxy, each optionally substituted by 1 to 5 halo;
b) halo, cyano, nitro, formyl, $C_{1-5}$ acyl;
c) $C_{2-3}$ alkynyl, $C_{2-3}$ alkenyl, each optionally substituted by 1 to 5 halo;
d) a group $S(O)_nR^7$ wherein n=0,1,2 and $R^7$ is $C_{1-4}$ alkyl, halo or $NR^8R^9$ wherein $R^8$ and $R^9$ are independently selected from hydrogen, $C_{1-4}$ alkyl and $C_{1-4}$ acyl;

and a group e) $NR^8R^9$ where $R^8$ and $R^9$ are as defined above;

$R^X$ is hydrogen or an optionally substituted $C_{1-8}$ alkyl or benzyl group, their preparation, pesticidal compositions containing them and their use against pests.

15 Claims, No Drawings

PENTA-2,4-DIENAMIDES AND USE AS PESTICIDES

This invention relates to pesticidal compounds, processes for their preparation, compositions containing them and to their use in the treatment of pests.

Insecticidal unsaturated amides have been described having a methylene chain of 1 to at least 10 carbon atoms optionally including an oxygen or additional methylene group having various terminating groups including optionally substituted phenyl (European Application Nos. 228222, 194764, 225011, Japanese Application No 57-212150, Maisters and Wailes: Aust. J. Chem. 1966, 19, 1215, Vi& et al : J. Ind. Chem. Soc. 1974, 51(9), 817), pyridyl (European Application 269457), fused bicyclic ring systems (European Application Nos. 143593, 228853), dihalovinyl or optionally substituted ethynyl (European Application 228222). Elliot et al : Pesticid. Sci. 1987, 18, 229 discloses structure-activity relationships of lipid amides of the above type, and found that when the N-alkyl terminus of the amide group is replaced by a N-phenyl terminus the activity is destroyed.

EP 369762A discloses that a cyclopropyl group interspersed between the diene unit and the terminating group favourably effects the insecticidal properties of such unsaturated amides.

It has now surprisingly been discovered that when the amide group of the above compounds is an optionally substituted anilide group, compounds result which have utility as pesticides with improved properties over those where the amide group is not an anilide.

Accordingly, the present invention provides a compound of formula (I):

$$Q(CH_2)_a(O)_bQ^1\ CR^2=CR^3\ CR^4=CR^5\ CXNR^1R^x$$

or a salt or propesticide thereof, wherein Q is an optionally substituted aromatic monocyclic or fused bicyclic ring system in which at least one ring is aromatic, or Q is a dihalovinyl group or a group $R^6-C\equiv C-$ where $R^6$ is $C_{1-4}$ alkyl, tri $C_{1-4}$ alkylsilyl, halo or hydrogen; $Q^1$ is a 1,2-cyclopropyl ring optionally substituted by one or more groups selected from $C_{1-3}$ alkyl, halo, $C_{1-3}$ haloalkyl, $C_{2-3}$ alkynyl, or cyano; or $Q^1$ is $(CH_2)_7$;

a=0 or 1; b=0 or 1;

$R^2$, $R^3$, $R^4$ and $R^5$ are the same or different with at least one being hydrogen and the others being independently selected from hydrogen, halo, $C_{1-4}$ alkyl or $C_{1-4}$ haloalkyl;

X is oxygen or sulphur;

$R^1$ is phenyl optionally substituted by 1-5 substituents chosen from:
a) $C_{1-4}$ alkyl, $C_{1-4}$ alkoxy, phenoxy and methylenedioxy, each optionally substituted by 1 to 5 halo;
b) halo, cyano, nitro, formyl, $C_{1-5}$ acyl;
c) $C_{2-3}$ alkynyl, $C_{2-3}$ alkenyl, each optionally substituted by 1 to 5 halo;
d) a group $S(O)_nR^7$ wherein n=0,1,2 and $R^7$ is $C_{1-4}$ alkyl, halo or $NR^8R^9$ wherein $R^8$ and $R^9$ are independently selected from hydrogen, $C_{1-4}$ alkyl or $C_{1-4}$ acyl;
and a group e) $NR^8R^9$ where $R^8$ and $R^9$ are as defined above;

$R^x$ is hydrogen or an optionally substituted $C_{1-8}$ alkyl or benzyl group.

A propesticide compound of formula (I) in which $R^x$ is replaced by $R^{x1}$, $R^{x1}$ is selected from:

(A)

where A is 0 or S, Y is phosphorus or carbon, D is hydrogen, $C_{1-4}$ alkyl, $C_{1-4}$ alkoxy, $C_{1-5}$ acyl or aryl or $CO_2D^1$ where $D^1$ is an $C_{1-4}$ alkyl or aryl, and a is 1 or 2

(B)

where b=0, 1 or 2 and $D^2$ is an (i) $C_{1-4}$ alkyl, aryl, aryloxy, or $C_{1-4}$ alkoxy, wherein an aryl ring may be substituted by one or more halo, nitro, cyano, $C_{1-4}$ alkyl, $C_{1-4}$ alkoxy groups each in turn optionally substituted by one or more halogens, or (ii) $D^2$ is a group $ND^3D^4$ wherein $D^3$ is $-COD^5$ where $D^5$ is hydrogen, fluorine or $C_{1-4}$ alkyl; or $D^3$ is $C_{1-4}$ alkyl substituted by $C_{1-5}$ acyl or aryl, carboalkoxy or cyano, or $D^3$ is a group $CO_2D^6$ where $D^6$ is $C_{1-4}$ alkyl or aryl; $D^4$ is hydrogen or $C_{1-4}$ alkyl.

Preferably $R^x$ is hydrogen or $C_{1-4}$ alkyl such as methyl or isopropyl or benzyl or a group (B) where b is 0 and $D^2$ is phenyl; or a group (A) where A is oxygen, and D is hydrogen or $C_{1-4}$ alkoxy.

Suitably $R^1$ is phenyl optionally substituted by 1 to 3 groups selected from alkyl, $C_{1-4}$ alkyl substituted by 1-5 halo, halo, $C_{1-4}$ alkoxy optionally substituted by 1-5 halo.

Suitably the substituents on the phenyl ring of $R^1$ are $C_{1-4}$ alkyl, halo or $C_{1-4}$ alkyl substituted by 1-5 halo. Preferably the substituents are methyl, ethyl, chloro, bromo, fluoro, or trifluoromethyl, fluoromethyl, difluoromethyl.

When Q is a ring system suitable substituents include:
a) $C_{1-6}$ hydrocarbyl, C alkoxy or methylenedioxy, each optionally substituted by 1-5 halo;
or b) halo, cyano, nitro formyl, $C_{1-5}$ acyl;
or c) $C_{2-3}$ alkynyl, $C_{2-3}$ alkenyl each optionally substituted by 1-5 halo;
or d) a group $S(O)_nR^7$ wherein n=0,1,2 and $R^7$ is $C_{1-4}$ alkyl, optionally substituted by one or more halos, halo or $NR^8R^9$ where $R^8$ and $R^9$ are independently selected from hydrogen, $C_{1-4}$ alkyl;
or e) a group $NR^8R^9$ where $R^8$ and $R^9$ are independently selected from hydrogen, $C_{1-4}$ alkyl or a group $COR^{10}$ where $R^{10}$ is $C_{1-6}$ alkyl or $C_{1-6}$ alkoxy.

Suitably when Q is a ring system it contains from 5 to 10 atoms containing a maximum of three heteroatoms selected from N, O or S and the rest carbon optionally substituted as defined above.

Suitably Q is phenyl, pyridyl, naphthyl or a fused bicyclic ring system containing a maximum of three hetero atoms selected from N, O or S, each optionally substituted, as defined above.

Preferably Q is a monocyclic aromatic ring or fused bicyclic ring system of which at least one ring is aromatic and containing 0 or 1 nitrogen atoms or 0 or 1 sulphur atoms.

When Q is a monocyclic aromatic ring, this is suitably phenyl, pyridyl thienyl and preferably phenyl. When Q is a bicyclic ring system, this is preferably naphthyl, quinolinyl, tetrahydronaphthyl or indanyl.

When Q contains an aromatic system, suitable substituents include:
  a) $C_{1-6}$ hydrocarbyl, $C_{1-6}$ alkoxy or methylenedioxy, each optionally substituted by 1-5 halo;
  b) halo, cyano, nitro formyl, $C_{1-5}$ acyl;
  c) $C_{2-3}$ alkynyl, $C_{2-3}$ alkenyl each optionally substituted by 1-5 halo;
  d) a group $S(O)_nR^7$ wherein n=0,1,2 and $R^7$ is $C_{1-4}$ alkyl, optionally substituted by one or more halos, halo or $NR^8R^9$ where $R^8$ and $R^9$ are independently selected from hydrogen $C_{1-4}$ alkyl;
  and e) a group $NR^8R^9$ where $R^8$ and $R^9$ are independently selected from hydrogen, $C_{1-4}$ alkyl or a group $COR^{10}$ where $R^{10}$ is $C_{1-4}$ alkyl or $C_{1-6}$ alkoxy.

The Q ring system normally contains up to three substituents and is suitably unsubstituted or substituted by one, two or three substituents such as halo or $C_{1-5}$ haloalkyl such as trifluoromethyl.

The substitution of the Q ring system depends upon the nature of this ring system but is preferably at the 3, 4 or 5 positions when Q is a 6-membered ring. Suitably $R^2$, $R^3$, $R^4$ and $R^5$ are chosen from hydrogen, methyl or fluoro. Suitably the stereochemistry of the double bonds is (E). Suitably when $R^3$ or $R^5$ is fluoro then the stereochemistry of the double bond to which $R^3$ or $R^5$ is attached is (Z).

Preferably $R^2$ is hydrogen, $R^3$ is hydrogen or fluoro, $R^5$ is hydrogen or fluoro and $R^4$ is hydrogen or $C_{1-4}$ alkyl, most preferably methyl.

Preferably $Q^1$ is a 1,2-cyclopropyl group or a group $(CH_2)_7$.

Preferably when $Q^1$ is a 1,2-cyclopropyl ring, b=0, a=0.

Preferably the stereochemical configuration of the cyclopropyl group in the chain is such that the groups Q and the carbon side-chain are attached to the ring at the 2- and 1- positions respectively to give trans geometry. Preferably the 3- position of the cyclopropyl ring is unsubstituted. Suitable substituents at the 1- and 2- positions of the cyclopropyl ring include hydrogen, fluoro, chloro, methyl or trifluoromethyl. Preferably the 2-position is unsubstituted and the 1-position is unsubstituted or substituted by fluoro or chloro.

Preferably $R^1$ is phenyl optionally substituted by one or more $C_{1-4}$ alkyl, halo or $C_{1-4}$ alkyl substituted by one or more halogens.

One suitable group of compounds of the formula (I) is that of the formula (II):

$$Q^a A^{1a} CR^{2a}=CR^{3a}CR^{4a}=CR^{5a}C(=X^a)NHR^{1a} \quad (II)$$

or a salt thereof, wherein $Q^a$ is an optionally substituted phenyl or pyridyl group or an optionally substituted fused bicyclic ring system of which at least one ring is aromatic and containing 0 or 1 nitrogen atoms or 0 or 1 sulphur atoms.

$Q^{1a}$ is a 1,2-disubstituted cyclopropyl ring optionally substituted by one or more groups selected from $C_{1-3}$ alkyl, halo, or $C_{1-3}$ haloalkyl; $R^{2a}$, $R^{3a}$, $R^{4a}$ and $R^{5a}$ are the same or different with at least one being hydrogen and the others being independently selected from hydrogen, halo, $C_{1-4}$ alkyl or $C_{1-4}$ haloalkyl; $X^a$ is oxygen or sulphur; $R^{1a}$ is selected from phenyl optionally substituted by halo and optionally substituted $C_{1-4}$ alkyl.

Suitable substituents for $Q^a$ include one or more groups selected from halo, cyano, nitro, $C_{1-6}$ alkyl, $C_{1-6}$ alkoxy and methylenedioxy, each optionally substituted by one or more halos or the substituent is a group $S(O)_nR^{7a}$ wherein n is 0, 1 or 2 and $R^{7a}$ is $C_{1-6}$ alkyl optionally substituted by halo.

Preferably $Q^a$ is substituted phenyl or naphthyl or pyridyl.

Suitably $R^{2a}$, $R^{3a}$, $R^{4a}$ and $R^{5a}$ are chosen from hydrogen, methyl, or fluoro. Preferably at most two are other than hydrogen.

Suitably $R^{1a}$ is selected from phenyl optionally substituted by one or more $C_{1-4}$ alkyl such as methyl, $C_{1-4}$ alkyl substituted by one or more halogens, such as trifluoromethyl, difluoromethyl or fluoromethyl, or halogen such as chloro, fluoro or bromo.

Preferred compounds of the formula (II) include those of formula (III):

$$Q^aQ^{1a}CH=CHCR^{4a}=CHCONHR^{1a} \quad (III)$$

wherein $Q^a$, $Q^{1a}$, $R^{4a}$ and $R^{1a}$ are as hereinbefore described.

One preferred group of compounds of the present invention includes those of formula (IV):

$$Q Q^1CH=CR^3CR^4=CR^5CONHR^1 \quad (IV)$$

wherein Q, $Q^1$, $R^4$, $R^3$, $R^5$ and $R^1$ are as hereinbefore described.

Preferred compounds of the formula (IV) include those wherein Q is substituted phenyl, $Q^1$ is a trans 1,2-disubstituted cyclopropyl ring, where the 1- position of the cyclopropyl ring is unsubstituted or substituted by fluoro or chloro, $R^4$ is methyl or hydrogen, $R^3$ and $R^5$ are hydrogen or fluoro and $R^1$ is phenyl optionally substituted by one or more $C_{1-4}$ alkyl and difluoromethyl, e.g. methyl, trifluoromethyl, difluoromethyl, fluoromethyl, chloro, fluoro, bromo.

By the term halo is meant fluoro, chloro, bromo and iodo. By the term hydrocarbyl group is meant, alkyl, alkenyl, alkynyl, aralkyl including a cyclic alkyl or alkenyl group optionally substituted by alkyl, alkenyl or alkynyl; and alkyl or alkenyl substituted by cyclic alkyl and alkenyl, and phenyl groups.

The term "acyl" as employed herein is taken to have the following meaning: COR wherein R is $C_{1-5}$ alkyl.

Salts of the compounds of the present invention will normally be acid addition salts. Such salts may be formed from mineral or organic or cycloalkyl acids. Preferred salts include those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methane- sulphonic, ethanesulphonic, benzenesulphonic, toluene-p-sulphonic, lactobionic, glucuronic, thiocyanic, propionic, embonic, naphthenoic and perchloric acids.

The compounds of formula (I) may exist in a number of stereoisomeric forms. The present invention encompasses both individual geometric and stereoisomers and mixtures thereof. The present invention also encompasses compounds of the formula (I) containing radioisotopes, particularly those in which one to three hydrogen atoms are replaced by tritium or one or more carbon atoms are replaced by $^{14}C$.

In a further aspect, the present invention provides processes for the preparation of a compound of the formula (I) as hereinbefore defined which comprises [Scheme 1]:

a) when X is oxygen, the reaction of the corresponding acid or acid derivative $Q(CH_2)_a(O)_bQ^1CR^2=CR^3CR^4=CR^5C(=X)Z^1$ with an amine $H_2NR^1$ wherein $Q,a,b,Q^1,R^2, R^3, R^4,R^5$, and $R^1$ are as hereinbefore defined and X is oxygen and $Z^1$ is hydroxy, $C_{1-6}$ alkoxy, halo or a phosphoroimidate ester $(-P(O)(O-aryl)NH-$ aryl where aryl is $C_{6-10}$ aryl)

b) the formation of the $CR^2=CR^3$ $CR^4aCR^5$ $C(=X^1)NHR^1$ moiety through a Wittig type reaction, and optionally thereafter converting one compound of the formula (I) into another compound of the formula (I) by methods well known to those skilled in the art.

Process (a) is normally carried out at a non-extreme temperature, for example between $-25°$ and $150°$ C. in an anhydrous aprotic solvent, such as ether, dichloromethane, toluene or benzene. The precise conditions will be dependent on the nature of the group $Z^1$, for example when $Z^1$ is alkoxy the reaction is conveniently carried out at an elevated temperature, i.e. $50°$ to $125°$ C., and conveniently at reflux, preferably in the presence of a trialkylaluminium compound, such as trimethylaluminium, which forms a complex with the amine $H_2NR^1$. When $Z^1$ is halo or phosphoroimidate the reaction is conveniently carried out at $-200°$ C. to $30°$ C. and preferably in the presence of a tertiary amine, such as triethylamine or pyridine.

If the acid derivative is an acid halide, for example the acid chloride, then it may be formed from the corresponding acid by reaction with a suitable reagent such as oxalyl chloride or thionyl chloride. When $Z^1$ is a phosphoroimidate group then this is suitably formed from $(PhO)P(\rightarrow O)NHPhCl$ where Ph is phenyl. The acid, or the acid function in the compound $Q(CH_2)_a(O)_bQ^1CR^2=CR^3CR^4=CR^5COZ^1$, may be prepared by hydrolysis of the corresponding ester.

The esters may be prepared by a number of alternative routes, for example [Scheme 2]:

(i) a conventional Wittig or Wadsworth-Emmons reaction, using for example an aldehyde and ethoxycarbonylmethylene triphenylphosphorane or an anion from triethylphosphonocrotonate or 3-methyl triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques. The Wittig-type reagent may be produced for example by the following route or a modification thereof:

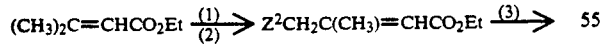

Wittig/Wadsworth-Emmons reagent (1) N-bromo succinimide
(2) e.g. $(EtO)_3P$ or $(Ph)_3P$
(3) a base such as lithium diisopropylamide, butyllithium, potassium carbonate sodium alkoxide or sodium hydride.
wherein $Z^2=(aryl)_3P, (aryl)_2P(O)$ or $(C_{1-4}$ alkoxy$)_2P(O)$ where aryl is preferably phenyl and alkoxy is preferably ethoxy.

(ii) by rearrangement and elimination of $HS(\rightarrow O)Z^3$ from a compound of formula:

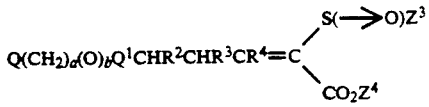

wherein $Q,Q^1,R^2,R^3$, a and b and $R^4$ are as hereinbefore defined, $Z^3$ is any suitable group, e.g. phenyl, substituted phenyl such as 4-chlorophenyl or $C_{1-4}$ alkyl, for example methyl, $Z^4$ is $C_{1-4}$ alkyl, e.g. methyl or ethyl.

The above compound may be obtained by reaction of a compound $Q(CH_2)_a(O)_bQ^1CHR^2CHR^3CR^4O$ with a compound $Z^3S(O)CH_2CO_2Z^4$.

(iii) By elimination of a compound

wherein $Q,a,b,Q^1, R^2, R^3,R^4,R^5$ and $Z^4$ are as defined above, and $Z^5$ is hydrogen or $C_{1-4}$ acyl such as acetyl. When $Z^5$ is acetyl the reaction is preferably carried out in an aromatic solvent, conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $Q(CH_2)_a(O)_bQ^1CR^2=CR^3C(=O)R^4$ with one of formula $Me_3SICHR^5CO_2Z^4$, wherein $Q,a,b,R^2$ to $R^5$, $Q^1$ and $Z^4$ are as hereinbefore defined.

This process may be carried out in an anhydrous solvent, e.g. tetrahydrofuran in the absence of oxygen, in the presence of a base, e.g. lithium cyclohexylisopropylamide.

(v) by reaction of a compound of formula $Q(CH_2)_a(O)_bQ^1CR^2=CR^3C(OZ^6)=CR^5CO_2Z^4$ with a compound of formula $R^4M^1$ wherein $Q,a,b,Q^1,R^2,R^3$, $R^4,R^5$ and $Z^4$ are as hereinbefore defined, $Z^6$ is a suitable group such as dialkylphosphate or trifluoromethanesulphonate and $M^1$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxygen.

(vi) by reaction of a compound of formula $Q(CH_2)_a(O)_bQ^1CR^2=CR^3M^2$ with one of formula Y $CR^4=CR^5CO_2Z^4$, wherein $Q,a,b,Q^1, R^2, R^3,R^4,R^5$ and $Z^4$ are as hereinbefore defined, Y is halo or tin and $M^2$ is a silyl or metal containing group, such as trimethylsilyl or a group containing zirconium, tin, aluminum or zinc, for example a bis(cyclopentadienyl) zirconium chloride group. This process is normally carried out at a non-extreme temperature i.e. between $0°$ and $100°$ C. and conveniently at room temperature, in a non-aqueous ethereal solvent such as tetrahydrofuran, in the presence of a palladium (O) catalyst, (such as bis (triphenylphosphine)palladium) and under an inert atmosphere of nitrogen or argon.

(vii) by elimination of $Z^3S (\rightarrow O)H$ from a compound of formula

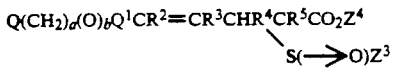

wherein Q,a,b,$Q^1$,$R^2$,$R^3$,$R^4$,$R^5$,$Z^3$ and $Z^4$ are as hereinbefore defined.

The above compound may be obtained by reaction of a compound $QQ^1CHR^2CR^3$=$CHR^4$ with $Z^3S(O)CHR^5CO_2Z^4$ Process (b) may be carried out by having an aldehyde or ketone group attached either to the amide/thioamide terminus or to the $QQ^1$ fragment of formula (I) and then reacting this with the appropriate phosphorous ylid. i.e. $Q(CH_2)_d(O)_bQ^1(CR^2$=$CR^3)COR^4 + Z^2CHR^5.C(=X)NHR^1$ or $Q(CH_2)_d(O)_bQ^1COR^2 + Z^2CHR^3.CR^4$=$CR^5.C(=X)NHR^1$ or $Q(CH_2)_d(O)_bQ^1(CR^2$=$CR^3)CHR^5Z^2 + R^5CO.C(=X)NH.R^1$
wherein Q,a,b,$Q^1$,$R^2$,$R^3$,$R^4$,$R^5$,$R^1$,X and $Z^2$ are as hereinbefore defined.

Process (b) is carried out in an anhydrous inert solvent, for example an ether such as tetrahydrofuran or an alcohol such as methanol, optionally in the presence of a base for the preparation of the phophorous ylid, and preferably in the absence of oxygen, e.g. under a nitrogen atmosphere, at a low temperature ($-60°$ to $20°$ c.). The phosphorous ylid may be obtained from its precursor as described above by reaction with a base such as lithium diisopropylamide, butyllithium, sodium alkoxide, potassium or sodium carbonate or sodium hydride. Compounds of the formula (I) wherein X is sulphur are preferably prepared by process (b) when $Z^2$ is a group ($C_{1-4}$ alkoxy)$_2$P=O.

Precursors of the type $Z^2CHR^3CR^4$=$CR^5(C$=$X^1)NHR$ are prepared according to the following route or a modification thereof when $X^1$- oxygen

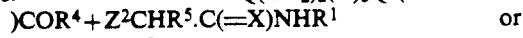

1) N-bromosuccinimide
2) thionyl chloride
3) $NH_2R^1$
4) $(EtO)_3P$ when $Z^2$=$-(OEt)_2P(O)-$ when $X^1$ is sulphur, precursors of the type $Z^2CHR^5(C$=$S)NHR^1$ are prepared from the reaction of the anion derived from $Z^2CH_2R$ with $R^1NCS$.

when $X^1$ is oxygen precursors of the type $Z^2CHR^5(C$=$O)NHR^1$ are prepared from the reaction of $Ph_3P$ or $P(OET)_3$ with $CLCHR^5(CO)NHR^1$.

The aldehyde intermediates $Q(CH_2)_d(O)_bQ^1CR^2$=$O$ may be prepared by acid hydrolysis of an appropriate protected precursor such as a ketal, enol ether or acetal in a solvent such as acetone-water or by oxidation of the appropriate alcohols using for example pyridinium chlorochromate, pyridinium dichromate, oxalyl chloride-dimethyl sulphoxide or N-acetylamido 2,2,6,6-tetramethylpiperidine-N-oxide and para toluene sulphonic acid in a solvent such as dichloromethane. The aldehydes may also be prepared by reduction of the appropriate nitriles with a reagent such as diisobutylaluminium hydride in hexane.

When Q is 1,2-disubstituted cyclopropyl ring the alcohols (Scheme 3) may be prepared by a) Reaction of $Q(CH_2)_d(O)_bCH$=$CX^2OH$ with $(Z^7)_2M^2$ and $CH_2X_2^3$ where $X^2$ is a group such as hydrogen, fluoro, chloro or methyl $X^3$ is a halogen such as iodine, $Z^7$ is $C_{1-4}$ alkyl group such as ethyl and $M^2$ a metal such as zinc, in an inert solvent such as hexane or dichloromethane at moderate temperature ($-20°$ C. to $+20°$ C). $CH_2$ and $CH$=$CX^2$ combine to form $Q^1$.

b) Reaction of $Q(CH_2)_d(O)_bCH$=$CX^2CH_2OH$ with $CX_2^4X^5CO_2M^3$ where $X^4$ and $X^5$ are halogens such as fluorine and chlorine and $M^3$ is an alkali metal such as sodium in an inert solvent such as diglyme at moderate/elevated temperature (150° C.-200° C.). $CX_2^4$ and $CH$=$CX^2$ combine to form $Q^1$.

The intermediate alcohols may be prepared by reduction of the ester $Q(CH_2)_d(O)_bCH$=$CX^2CO_2Z^4$ with for instance diisobutylaluminium hydride in an inert solvent such as dichloromethane or tetrahydrofuran at moderate temperature ($-20°$ C. to $25°$ C.).

c) Reduction of an ester $Q(CH_2)_d(O)_bQ^1CO_2Z^4$, or of the appropriate carboxylic acid with for instance diisobutylaluminium hydride, lithium aluminium hydride, or sodium borahydride or diborane in an inert solvent such as dichloromethane ) ethanol or tetrahydrofuran at moderate temperature ($-20°$ C. to $25°$ C.). The esters may be prepared by reaction of a diazoacetate $N_2CH.CO_2Z^4$ with a compound $Q(CH_2)_d(O)_bCH$=$CH_2$ in the presence of a copper containing catalyst such as copper sulphate where CH and $CH$=$CH_2$ combine to form $Q^1$. The esters may also be prepared by the reaction of $Q(CH_2)_d(O)_bCH$=$CHCO_2Z^4$ with an anion derived from $Me_2S(O)_mC(Z^7)_2$ where $Z^7$ is hydrogen or $C_{1-6}$ alkyl and m is 1 or 2.

The attached reaction schemes assist in illustrating the preparation of the intermediates and their conversion to compounds of formula (1).

The intermediates of the present invention form a further aspect of the present invention and may be prepared where appropriate by standard methods other than those described.

The compounds of formula (I) may be used to control pests such as arthropods e.g. insect and acarine pests, and helminths, e.g. nematodes or molluscs e.g. slugs. Thus, the present invention provides a method for the control of arthropods and/or helminths and/or molluscs which comprises administering to the arthropod and/or helminth and/or molluscs or to their environment an amount of a compound of the formula (I) sufficient to control the pest. The present invention also provides a method for the control and/or eradication of arthropod and/or helminth and/or mollusc infestations of animals (including humans) and/or of plants,(including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids) and termites.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods or helminths or molluscs which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the plants, animals or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% W/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately $35 \times 22 \times 3$mm dimensions, treated with up to 0.3ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The compounds of formula (I) are of use in the protection and treatment of plant species, in which case an effective insecticidal, acaricidal, molluscidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3kg/Ha and preferably between 0.01 and 1kg/Ha. Typical formulations for agricultural use contain between 0.0001% and 50% of a compound of formula (I) and conveniently between 0.1 and 15% by weight of a compound of the formula (I).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20ppm. Space sprays may be applied to give an average initial concentration of 0.001 to 1 mg of compound of formula (I) per cubic meter of treated space.

Dusts, greases, pastes and aerosol formulations are usually applied in a random fashion as described above and concentrations of 0.001 to 20% w/v of a compound of Formula (1) in the applied formulation may be used.

The compounds of formula (I) have been found to have activity against the common housefly (*Musca domestics*). In addition, certain compounds of formula (I) have activity against other arthropod pests including *Myzus persicae, Tetranychus urticae, Spodoptera Littoralis, Heliotuis virescens, Plutella xylostella, Culex* spp. *Tribolium castaneum, Sitophilus granarius, Periplaneta americana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. *Anobium, Ceuthorrhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus* or *Anthrenus* Spp.), Lepidoptera (e.g. *Ephestia, Mamestra, Earias, Pectinophora, Ostrinia, Trichoplusia, Pieris, Laphygma,, Agrotis, Amathes, Wiseana, Tryporyza, Diatraea, Sparganothis, Cydia, Archips, Plutella, Chilo, Heliothis, Spodoptera Littoralis, Helrotuis virescens, Spodoptera* or *Tineola* spp.), Diptera (e.g. *Musca, Aedes, Anopheles, Culex, Glossina, Simulium, Stomoxys, Haematobia, Tabanus, Hydrotaea, Lucilia, Chrysomyia, Callitroga, Dermatobia, Gasterophilus, Hypoderma, Hylemyia, Atherigona, Chlorops, Phytomyza, Ceratitis, Liriomyza* and *Melophagus* spp.), Phthiraptera (*Mallophaga* (e.g. *Damalina* spp.), *Anoplura* (e.g. *Linognathus* and *Haematopinus* spp.), Hemiptera (e.g. *Aphis, Bemisia, Phorodon, Aeneolamia, Empoasca, Parkinsiella, Pyrilla, Aonidiella, Coccus, Pseudococcus, Helopeltis, Lygus, Dysdercus, Oxycarenus, Nezara, Aleyrodes, Triatoma, Psylla, Llyzus, Megoura, Phylloxera, Adelges, Nilaparvatal Nephotettix* or *Cimex* spp.), Ortboptera (e.g. *Locusts, Gryllus, Schistocerca* or *Acheta* spp.), Dictyoptera (e.g. *Blattella, Periplaneta* or *Blatta* spp.), Hymenoptera (e.g. *Athalia, Cephus, Atta, Solenopsis* or *Monomorium* spp.), Isoptera (e.g. *Odontotermes* and *Reticulitermes* spp.), Siphonaptera (e.g. *Ctenocephalides* or *Pulex* spp.), Thysanura (e.g. *Lepisma* Spp.), Dermaptera (e.g. *Forficula* spp.), Psocoptera (e.g. *Peripsocus* spp.) and Thysanoptera (e.g. *Thrips tabaci*),.

Acarine pests include ticks, e.g. members of the genera *Boophilus,Ornithodorus, Rhipicephalus, Amblyomma, Hyalomma, Ixodes, Haemiphysalis, Dermacentor* and *Anocentor,* and mites and manges such as *Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerelia,* and *Oniscus* spp.

Nematodes which attack plants and trees of importance to agriculture, forestry, horticulture either directly or by spreading bacterial, viral, mycoplasma or, fungal diseases of the plants, include root-knot nematodes such as *Meloidogyne* spp. (e.g. *M. incognita*); cyst nematodes such as *Globodera* spp. (e.g. *G. rostochiensis*); *Heterodera* spp. (e.g. *hydrogen avenae*); *Radopholus* spp. (e.g. *R. similes*); lesion nematodes such as *Pratylenchus* spp. (e.g. *P. pratensis*); *Belonolaimus* spp. (e.g. *B. graci-* lis); *Tylenchulus* spp. (e.g. *T. semipenetrans*); *Rotylenchulus* spp. (e.g. *R. reniformis*); *Rotylenchus* spp. (e.g. *R. robustus*); *Helicotylenchus* spp. (e.g. *hydrogen. multicinctus*);*Hemicycliophora* spp. (e.g. *hydrogen. gracilis*); *Criconemoides* spp. (e.g. *C. similes*); *Trichodorus* spp. (e.g. *T primitivus*); dagger nematodes such as *Xiphinema* spp. (e.g. *X. diversicaudatum*), *Longidorus* spp (e.g. *L. elongatus*); *Hoplolaimus* spp. (e.g. *hydrogen. coronatus*); *Aphelenchoides* spp. (e.g. *A. ritzema-bosi, A. besseyi*): stem and bulb eelworms such as *Ditylenchus* spp. (e.g. *D. dirsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1-1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

INDUSTRIAL APPLICABILITY

Compounds of the present invention show increased pesticidal properties and/or photostability and/or reduced mammalian toxicity.

The following examples illustrate, in a non-limiting manner, preferred aspects of the invention.

| Formulations | |
|---|---|
| 1. Emulsifiable Concentrate | |
| Compound of formula (I) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |
| 2. Emulsifiable Concentrate | |
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |
| Antioxidant | 3.00 |
| | 100.00 |
| 3. Wettable Powder | |
| Compound of formula (I) | 5.00 |
| $C_{8-13}$ aromatic solvent | 7.00 |
| $C_{18}$ aromatic solvent | 28.00 |
| China clay | 10.00 |
| Alkyl aryl sulphonate* | 1.00 |
| Napthalene sulphonic acid* | 3.00 |
| Diatomaceous earth | 46.00 |
| | 100.00 |
| 4. Dust | |
| Compound of formula (I) | 0.50 |
| Talc | 99.50 |
| | 100.00 |
| 5. Bait | |
| Compound of formula (I) | 0.5 |
| Sugar | 79.5 |
| Paraffin wax | 20.0 |
| | 100.00 |
| 6. Emulsion Concentrate | |
| Compound of formula (I) | 5.00 |
| $C_{8-13}$ aromatic solvent | 32.00 |
| Cetyl alcohol | 3.00 |
| Polyoxyethylene glycerol monooleate* | 0.75 |
| Polyoxyethylene sorbitan esters* | 0.25 |
| Silicone solution | 0.1 |
| Water | 58.9 |
| | 100.00 |
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| $C_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| $C_{8-13}$ saturated hydrocarbon solvent | 58.2 |
| Butane | 40.0 |
| | 100.00 |
| 12. Aerosol (pressure pack) | |
| Compound of formula (I) | 0.3 |
| $C_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| $CO_2$ | 3.00 |
| Polyoxyethylene glycerol monooleate* | 1.40 |
| Propanone | 38.00 |
| Water | 56.60 |
| | 100.00 |
| 14. Lacquer | |
| Compound of formula (I) | 2.50 |
| Resin | 5.00 |
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |
| Odourless kerosene | 99.8 |
| | 100.00 |
| 16. Potentiated Spray (ready to use) | |

| Formulations | |
|---|---|
| Compound of formula (I) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| $C_{8-13}$ aromatic solvent | 10.0 |
| Aromatic di-isocyanate# | 4.5 |
| Alkyl phenol ethoxylate* | 6.0 |
| Alkyl diamine | 1.0 |
| Diethylene triamine | 1.0 |
| Concentrated hydrochloric acid | 2.2 |
| Xanthan gum | 0.2 |
| Fumed silica | 0.5 |
| Water | 64.6 |
| | 100.00 |
| 18. Dispersible Concentrate | |
| Compound of formula (I) | 5.0 |
| N-methyl pyrrolidinone | 15.00 |
| N-alkyl pyrrolidinone | 53.00 |
| $C_8$-$C_{13}$ aromatic solvent | 16.00 |
| Polyoxyethylene nonyl phenyl ether phosphate | 6.00 |
| Alkyl phenyl ethoxylate | 3.50 |
| Alkyl ary sulphonate | 1.30 |
| Polyalkylene glycol ether | 0.20 |
| | 100.00 |

*Surfactant
react to form the polyurea walls of the microcapsule
Antioxidant could be any of the following individually or combined
Butylated hydroxytoluene
Butylated hydroxyanisole Vitamin C (ascrobic acid)

The following Examples illustrate, in a non-limiting manner, preferred aspects of the invention.

EXPERIMENTAL

General Synthetic Methods and Procedures

Various compounds were synthesised and characterised in accordance with the following experimental procedures.

$^1$H NMR spectra were obtained on a Bruker AM-250 spectrometer in deuterochloroform solutions with tetramethylsilane as internal standard and are expressed as ppm from TMS, number of protons, number of peaks, coupling constant J Hz.

Progress of reactions could also be conveniently monitored on Aluminium sheets (40×80mm) precoated with 0.25 mm layers of silica gel with fluorescent indicator and developed in appropriate solvent or solvent mixture. Temperatures are in degrees Celsius throughout.

Diethyl ether, hexane, ethanol, methanol, triethylamine, pyridine, magnesium sulphate and sodium hydroxide were obtained from BDH. Dichloromethane was obtained from Romil Chemicals and diemethylformamide from Rathburn Chemicals Ltd. The source of other chemicals is indicated in the text.

EXAMPLE A ($\pm$)-(2E,4E)-N-Phenyl-5-[c-2-(3,4-dibromophenyl)-r-1-fluorocyclopropyl]penta-2,4-dienamide (1)

(i) (Z)-Ethyl 3-(3,4-dibromophenyl)-2-fluoroprop-2-enoate was prepared by an analogous method to example 24 (EP0369762 Al) from 3,4-dibromobenzaldehyde (example 14 EP0369762 Al). NMR $^1$H: 1.2(3H,t), 4.3(24,q), 6.6(1H,d), 7.4(3H,m).

(ii) Ethyl ($\pm$)-5-[c-2-(3,4-dibromophenyl)-r-1-fluorocyclopropyl]penta-2,4-dienoate was prepared from the above by an analogous method to example 1 (EP0369762 Al) using triethyl 4-phosphonocrotonate (ex Lancaster). NMR $^1$H: 1.3(3H, t), 1.6(1H,m), 2.3(1H,m), 4.2(2H,q), 5.8(1H,d), 5.9(1H,dd), 6.4(1H,dd), 7.0(1H,m), 7.3(1H,dd), 7.5(2H,m).

(iii)Ethyl ($\pm$)-5-[c-2-(3,4-dibromophenyl)-r-1-fluorocyclopropyl]penta-2,4-dienoate (3.5 g) in ethanol (50 ml) was stirred and heated to 50° C. A solution of sodium hydroxide (0.8 g) in water (5 ml) was added and heating continued for a further three hours. The solvent was removed under vacuum and water and diethyl ether were added. The aqueous solution was separated and acidified with dilute hydrochloric acid. The precipitate was extracted with diethyl ether, washed with brine and dried over magnesium sulphate. Removal of the solvent under vacuum gave ($\pm$)-5-(C-2-(3,4-dibromophenyl)-r-1-fluorocyclopropyl]penta-2,4-dienoic acid (2.5 g). NMR 1H: 1.5(1H,m), 1.8(1H,m), 2.3(1H,m), 5.9(2H,m), 6.4(1H,dd), 7.0(1H,m), 7.3(1H,dd), 7.5(2H,m).

(iv) The above acid (360 mg) was suspended in dichloromethane (15 ml) and stirred under nitrogen at room temperature while oxalyl chloride (ex Aldrich) (156 mg/107 µl) and dimethylformamide (1 drop) were added. Stirring was continued for two hours and the solvent removed in vacuo. The remaining solid was dissolved i-n dichloromethane (20 ml) and triethylamine (123 mg/170 µl) and aniline (ex Aldrich) (114 mg/112 µl) were added. After stirring overnight the organic solution was washed successively with 2N hydrochloric acid, saturated sodium hydrogen carbonate, brine and dried over magnesium sulphate. Removal of the solvent under vacuum gave after crystallisation from methanol the title compound (75 mg). M.pt 174°-5° C. NMR (DMSO) $^1$H: 1.7(1H,m), 2.1(1H,m), 2.6(1H,m), 6.3(2H,m), 6.5(1H,dd), 7.1(1H,dd), 7.5(4H,m).

Compounds 1-3 were prepared in an analogous manner, using the Wittig reagent and aniline as specified.

EXAMPLE B ($\pm$)-(2E,4E)-N-Phenyl-5-[c-2-(3,4-dibromophenyl)-r-1-fluorocyclopropyl]-3-methylpenta-2,4-dienamide (2)

(i) Ethyl ($\pm$)-5-[c-2-(3,4-dibromophenyl)-r-1-fluorocyclopropyl]-3-methylpenta-2,4-dienoate was prepared using triethyl 3-methyl-4-phosphonocrotonate (ex Lancaster) as described in example A(ii) above. NMR $^1$H: 1.3(3H,t), 1.6(1H,m), 1.8(1H,m), 2.0 and 2.3(3H,s), 2.3(1H,m), 4.2(2H, q), 6.0 and 7.8(3H,m), 7.0(1H,m), 7.5(2H,m).

(ii) The above ester was hydrolysed using the conditions described in example A(iii) to give ($\pm$)-5-[c-2-(3,4-dibromophenyl)-r-1-fluorocyclopropyl]-3-methylpenta-2,4-dienoic acid. NMR $^1$H: (1.6(1H,m), 1.8(1H,m), 2.1 and 2.3(3H,s), 2.3(1H,m), 5.7 and 5.8(1H,s), 6.0(2H,m), 6.4 and 7.8(1H,m), 7.0(1H,m), 7.5(2H,m).

(iii)The above acid (3.0 g) was suspended in dry dichloromethane (50 ml) and stirred under nitrogen at 0° C. while oxalyl chloride (840 µl) and dimethyl formamide (1 drop) were added. Stirring was continued for two hours and the solvent removed in vacuo. Dichloromethane (100 ml) was added and the solution stirred at −20° C. under nitrogen. Pyridine (790 µl) and aniline (880 µl) were added and stirring continued for a further seventeen hours. Water and dichloromethane were added and the organic phase separated and washed successively with 2N hydrochloric acid, saturated sodium hydrogen carbonate and brine, and dried over magnesium sulphate. After filtration, the filtrate was evaporated under reduced pressure to give a solid (3.0 g).

Purification by chromatography (silica, ether/hexane) yielded the title compound (1.1 g). M.Pt. 138° C.. NMR ¹H: 1.6(1H,m), 1.8(1H,m), 2.3(1H,m), 2.4(3H,s), 5.8(2H,m), 6.4(1H,d), 7.5(8H,m).

(±)-(2E,4E)-N-2-Methylphenyl 5-[c-2-(3,4-dibromophenyl)-r-1-fluorocyclopropyl]-penta-2,4-dienamide (19)

(±)-5-[c-2-(3,4-Dibromophenyl)-r-1-fluorocyclopropyl]penta-2,4-dienoic acid (Prepared as in example A) (132 g) in dichloromethane (51) was treated with oxalyl chloride (56 g) and dimethylformamide (10 drops) (cF. example A). After the volatiles had been removed the acid chloride was dissolved in dry dichloromethane (51) and the solution cooled to −1° C. Pyridine (34 g) was added and five minutes later o-toluidine (46 g). The mixture was left at room temperature overnight. The reaction mixture was diluted with hexane and the said product collected by filtration, washed with hexane and dried in vacuo. The crude product triturated with warming with isopropanol, collected by filtration, washed with hexane and dried to give the title compound (258 g).

(±)-(2E,4E)-N-2-Methylphenyl 5-[c-2-(3,4-dichlorophenyl)-r-1-fluorocyclopropyl]-penta-2,4-dienamide (68)

(±)-5-[c-2-(3,4-Dichlorophenyl)-r-1-fluorocyclopropyl]penta-2,4-dienoic acid was prepared by analogy with example A starting from 3,4-dichlorobenzaldehyde (ex. Aldrich). The above acid (1 g) in dichloromethane was treated with oxalyl chloride (0.36 ml) and dimethylformamide (2 drops). The acid chloride in dichloromethane was treated with pyridine (0.34 ml) and o-toluidine (0.44 g) at -10° C. Upon completion the reaction was worked up as described previously and the crude product washed with ether:hexane and dried in vacuo to give the title compound (0.64 g).

Compound 1 and 4–85 were prepared in an analogous manner, using the Wittig Reagent and aniline as specified (Table 1).

EXAMPLE C (±)-(2-E,4E-)-N-2-Methylphenyl 5-[c-2-(3,4-dibromophenyl)-r-fluorocyclopropyl]-penta-2,4-dienamide (19)

N-2-Methylphenyl diethyl 4-phosphonocrotonamide (i) N-Bromosuccinimide (136 g) and benzoyl peroxide (1 g) mixed together and added in four portions to crotonic acid (60 g) in tetrachloromethane (400 ml) heated under reflux. After heating for two hours the cooled mixture was treated with dilute hydrochloric acid and the organic layer separated, dried and concentrated to give 4-bromocrotonic acid (35 g).

(ii) 4-Bromocrotonic acid (98 g) and thionyl chloride (250 ml) stirred at room temperature for 18 hours and volatiles removed to give 4-bromocrotonyl chloride (107 g).

(iii) 4-Bromocrotonyl chloride (30 g) in dry ether added to a solution of pyridine (14.3 g) and o-toluidine (22.8 g) in ether at 0° C. with efficient stirring.

(iv) N-2-Methylphenyl 4-bromocrotonamide (20 g) and triethylphosphite (16.7 g) heated together at 140° C. and the bromoethane produced removed by distillation. The crude product was purified by chromatography on silica (5% ethanol in ethyl acetate) to give the phosphonocrotonamide as a colourless solid (mp. 84° C.) NMR ¹H: 7.83(1H,s), 7.71(1H), 7.16,7.09(3H,2m), 6.82(1H,s), 6.07(1H,d-of-d), 2.22(3H,s), 1.36(6H,t).

3,4-Dibromophenyl-1-fluorocyclopropyl]methanal (prepared from 3,4-dibromobenzaldehyde by analogy with examples cited in EP 369762) (2.5 g) was added to a mixture of the aforementioned phosphonocrotonamide (3.63&) and potassium carbonate (1.38 g) in methanol (100 ml). The reaction mixture was allowed to stir at room temperature for 2 days and diluted with water. The solid product was collected by filtration, dried, washed with hexane and dried in vacuo to give the title compound (1.88 g).

Or

A solution of lithium diisopropylamide in dry tetrahydrofuran was prepared from n-butyl lithium in hexane (2.58 ml at 1.6 M¹) and diisopropylamine (0.63 ml). This was treated as the aforementioned phosphonocrotonamide (1.24 g) in tetrahydrofuran at −78° C. for 2 hours. 2-(3,4-Dibromophenyl)-1-fluorocyclopropyl methanal (1.21 g) was added. After 18 hours at room temperature dilute aqueous hydrochloric acid was added and the crude product collected by filtration. The latter was triturated with warm isopropanol, filtered off and dried in vacuo to give the title compound (1.73 g).

EXAMPLE D (±)-(2E,4E)-N-(2-fluoromethylphenyl)-5-fc-2-(3,4-dibromophenyl)-r-1-fluorocyclopropyl]penta-2,4-dienamide (86)

A solution of compound 64 (100 mg, 0.2 mmol) in dichloromethane (10 ml) was added dropwise to a stirred solution of diethylaminosulphurtrifluoride (0.05 ml, 0.2 mmol) in dichloromethane (5 ml) at −78° C. under nitrogen. The reaction mixture was stirred for 4.5 hours allowing to warm to room temperature. The reaction mixture was added to water (50 ml) and the organic layer was dried (magnesium sulphate). Evaporation of the solvent gave a dark brown solid which was tritrated with ether to yield the title compound as a pale brown solid (12 mg, 12%) M.pt.=163°-165° C., m 566. NMR DMSO ¹H: 1.6(1H,m), 2.1(1H,m), 2.5(1H,m), 5.4(2H,d), 6.4(3H,m), 7.4(8H,m), 9.7(1H,s).

EXAMPLE E (±)-(2E,4E)-N-(2-Hydroxyphenyl)-5-[c-2-(3,4-dibromophenyl)-r-1-fluorocyclopropyl]penta-2,4-dienamide (87)

(i) Imidazole (3.73 g) was added in one portion to a solution of 2-aminophenol (2.0 g) in dry dimethylformamide (10 ml) stirred at 25° C. under nitrogen. Chlorotrimethylsilane (2.98 g) was added dropwise over 5 minutes and stirring continued for a further 18 hours. The mixture was poured onto water (30 ml) and extracted with diethyl ether (2×60 ml). The organic solution was separated and washed with 2N sodium hydroxide (2×40 ml), brine and dried over magnesium sulphate. Evaporation of the filtrate under reduced pressure gave an oil. Column chromatography on silica eluting with 10% ether:hexane gave 2-trimethylsilyloxyaniline (0.85 g). NMR ¹H: 0.2(9H,s), 3.5(2H,s), 6.4(4H,m).

(ii) The corresponding amide of (±)-(2E,4E)-5-[c-2-(3,4-dibromophenyl)-r-1-fluorocyclopropyl]penta-2,4-dienoic acid was obtained by the procedure described in example B(iii).

(iii) Tetrabutylammonium fluoride (1M solution in tetrahydrofuran; 1.5 ml) was added over 5 minutes to a stirred solution of the above (550 mg) in tetrahydrofuran (10 ml) kept at room temperature under nitrogen. Stirring was continued for a further 18 hours when diethyl ether (50 ml) and water (40 ml) was added. The organic solution was separated, washed with brine and dried (magnesium sulphate). Evaporation of the filtrate under reduced pressure gave the crude product. Chromatography on silica eluting with diethyl ether:hexane gave the title compound (87) (92 mg).

EXAMPLE F (1) Separation of enantiomers Ethyl (±)-(2E,4E)-5-[c-2-(3,4-dibromophenyl)-r-1-fluorocyclopropyl]penta-2,4-dienoate Enantismers of the above compound were separated using preparative hplc on a chiralcell OD (25×200 mm) column. Multiple injections (5 ml) of the above ester (800 mg) in warm isopropyl alcohol (2% solution) were made. The mobile phase was 6% isopropyl alcohol:hexane eluting at a flow rate of 9 ml/min. Fractions were combined and collected at 27min., [α] = +304.4° (300 mg), (Fraction A) and at 46 min., [α] = −272°-9° (300 mg) (Fraction B). Separation of the enantiomers of the above compound can be achieved as described in U.S. Ser. No. 07/811,439.

(ii) (±)-(2E,4E)-N-(2-Methylphenyl)-5-[(1S,2R)-2-(3,4-dibromophenyl)-1-fluorocyclopropyl]penta-2,4-dienamide (88)

The above fraction A was hydrolysed using the conditions described in example A(iii) to give the corresponding acid [α]− +280.50°. Treatment with o-toluidine using the conditions described in example B(iii) gave the title compound (68 mg), m.pt. 185°-6° C., [α] = +263.2. NMR $^1$H: 1.5(1H,m), 1.8(1H,m), 2.4(1H,m), 2.4(3H,s), 5.9(2H,m), 6.5(1H,dd), 7.0–8.0(9H,m).

(iii) (−)-(2E,4E)-N-(2-Methylphenyl)-5-[(1R,2S)-2-(3,4-dibromophenyl)-1-fluorocyclopropyl]penta-2,4-dienamide (89)

The fraction B was hydrolysed using the conditions described in example A(iii) to give the corresponding acid [α] = −276.8° C. Treatment with o-toluidine using the conditions described in example B(iii) gave the title compound (250 mg), m.pt. = 174°-6° C. NMR $^1$H: 1.5(1H,m), 1.8(1H,m), 2.4(1H,m), 2.4(3H,s), 5.9(2H,m), 6.5(1H,dd), 7.0–8.0(9H,m).

EXAMPLE G (±)-(2E,4E)-N-(2-Methylphenyl)-5-[r-1-chloro-c-(3,4-dichlorophenyl)cyclopropyl]-3-methylpenta-2,4-dienamide (90)

Ethyl (±)-(2E,4E)-3-methyl[r-1-chloro-c-(3,4-dichlorophenyl)cyclopropyl]penta-2,4-dienoate was prepared as described in EP 0 369 762 A1 example 25. The above ester was converted into the title compound by analogy with example B(ii) and (iii). m.pt. = 170.6° C. NMR $^1$H: 1.8(2H,m), 2.3(3H,s), 2.4(3H,s), 2.5(1H,m), 5.9(2H,m), 6.5(1H,d), 6.9–8.0(8H,m).

Compounds 91–95 were made in an analogous manner starting from the appropriate aldehyde.

EXAMPLE H (±)-(2Z-4E)-N-(2-Methylphenyl)-5-[c-2-(3,4-dibromophenyl)-r-1-fluorocyclopropyl]-2-fluoro-3-methylpenta-2,4-dienamide (96)

(±)-c-2-(3,4-Dibromophenyl)-r-1-fluorocyclopropylmethanal (example A) was treated as described in EP 0 369 762 A1 example 23 to give ethyl (±)-(2Z,4E)-5-[c-2-(3,4-dibromophenyl)-r-1-fluorocyclopropyl]-2-fluoro-3-methylpenta-2,4-dienoate. The above ester was converted to the title compound by analogy with example B(ii) and (iii). m.pt. = 104°-5° C., m+$^1$ 510. NMR $^1$H: 1.6(2H,m), 1.8(1H,m), 2.3(3H,s), 2.4(3H,d), 5.9(1H,dd), 6.9(1H,d), 7.0–8.0(8H,m).

(±)-(2Z,4E)-N-(2-Chlorophenyl)-5-[c-2-(3,4-dibromophenyl)-r-1-fluorocyclopropyl]-2-fluoro-3-methylpenta-2,4-dienamide (97). M.pt. = 128°-9° C., M+$^1$ 530 was made in an analogous manner. NMR $^1$H: 1.6(1H,m), 1.9(1H,m), 2.3(1H,m), 2.4(3H,s), 5.9(1H,dd), 6.9(1H,d), 7.0–7.6(7H,m), 8.6(1H,m).

EXAMPLE I (±)(2Z,4E)-N-(2-Methylphenyl)-5-[c-2-(3,4-dichlorophenyl)-r-1-fluorocyclopropyl]-2-fluoropenta-2,4-dienamide (98)

Ethyl 2-fluorocrotonate (6.0 g) (prepared according to E. D. Bergmann and I. Shahak, J.Chem.Soc., 4033, 1961) N-bromosuccinimide (8.1 g) and benzoyl peroxide (0.15 g) was dissolved in carbon tetrachloride (120 ml) and heated at reflux for 3–5 hours. The mixture was cooled, filtered and the filtrate evaporated to dryness under reduced pressure. Chromatography on silica eluting with 10% diethyl ether: hexane gave ethyl 4-bromo-2-fluorocrotonate as a yellow oil (7.6 g). NMR $^1$H: 1.5(3H,t), 4.1(2H,dd), 4.4(2H,q), 6.4(1H,dt).

The above ester (7.6 g) and triethyl phosphite (6.6 g/7.0 ml) were heated under distillation conditions at 140°-5° C. until ethyl bromide ceased to distil over. Heating was continued for a further 1 hour at 150° C. and the solution cooled. Chromatography on silica eluting with diethyl ether yielded after evaporation triethyl 2-fluoro-4-phosphonocrotonate (4.6 g), M+$^1$ 167. NMR $^1$H: 1.5(9H,t), 2.9(2H,ddd), 4.4(6H,m), 6.4(1H,ddt).

A solution of n-butylithium (3.0 ml) (1.6M, hexane) was added to a stirred solution of diisopropylamine (0.66 ml) in dry tetrahydrofuran (40 ml) kept at −10° C. under nitrogen. After 30 minutes the solution was cooled to −40° C. and a solution of triethyl 2-fluoro-4-phosphononate (1.26 g) in dry tetrahydrofuran (10 ml) was added. The solution warmed to room temperature over 1.5hours and a solution of (±)-c-2-(3,4-dichlorophenyl)-r-1-fluorocyclopropylmethanol (0.89 g) (example B) in dry tetrahydrofuran (10 ml) was added. After stirring for 18 hours, water was added and the mixture worked up in the normal manner. Chromatography on silica eluting with 30% diethyl ether:hexane gave ethyl (±)-(2Z,4E)-5-[c-2-(3,4-dichlorophenyl)-r-1-fluorocyclopropyl]-2-fluoropenta-2,4-dienoate as a colourless oil (1.23 g), NMR $^1$H: 1.4(3H,t), 1.5–2.5(3H,m), 4.4(2H,q), 5.8–7.6(3H,m).

The above ester was converted into the title compound by analogy with example B(ii) and (iii). m+$^1$ 408 NMR $^1$H: 1.7(1H,m), 2.0(1H,m), 2.2(3H,s), 2.6(1H,m), 6.3(1H,dd), 6.5(1H,dd), 6.8(1H,dd), 7.1–7.6(7H,m), 9.8(1H,s).

Compounds 99-101 were prepared in an analogous manner, using the parent substituted benzaldehyde and aniline.

EXAMPLE J (±)-(2E,4E)-N-(2-Methylphenyl)-5-[trans-2-(3,4-dibromophenyl)cyclopropyl]-3-methylpenta-2,4-dienamide (102)

The preparation of ethyl (±)-(2E,4E)-5-[trans-2-(3,4-dibromophenyl)cyclopropyl]-3-methylpenta-2,4-dienoate is described in EP 0 369 762 Al example 14. The above ester was converted to the title compound by analogy with example B(ii) and (iii) M+1 474. NMR 1H: 1.3(2H,m), 1.8(1H,m), 2.0(1H,m), 2.3(3H,s), 2.4(3H,s), 5.7(2H,m), 6.2(1H,d), 6.9-8.0(8H,m).

(±)-(2E,4E)-N-(2-Methylphenyl)-5-[trans-2-(3,4-dibromophenyl)cyclopropyl]penta-2,4-dienamide (compound 103) was prepared similarly m.pt.=165° C., M+1 460. NMR 1H: 1.3(2H,m), 1.8(1H,m), 2.0(1H,m), 2.4(3H,s), 5.7(1H,dd), 6.0(1H,d), 6.3(1H,dd), 6.9(1H,d), 7.0-8.0(8H,m).

EXAMPLE K (−)-(2E,4E)-N-(2-Methylphenyl)-5-[(1R,2S)-trans-2-(3,4-dibromophenyl) cyclopropyl]-3-methylpenta-2,4-dienamide (104)

(−) Ethyl 5-[trans-2-(3,4-dibromophenyl)cyclopropyl]-3-methylpenta-2,4-dienoate was prepared in an analogous manner to that described for EP 0 369 762 Al example 12. The above ester was converted to the title compound by analogy with example B(ii) and (iii). $\alpha_D^{20}$ = −124° C. NMR 1H: 1.3(2H,m), 1.8(1H,m), 2.0(1H,m), 2.3(3H,S), 2.4(3H,s), 5.7(2H,m), 6.2(1H,d), 6.9-8.0(8H,m).

(+)-(2E,4E)-N-(2-Methylphenyl)-5-[trans-2-(3,4-dibromophenyl)cyclopropyl]-3-methylpenta-2,4-dienamide (compound 105) was obtained analogously [EP 0 369 762 Al example 12]. $\alpha_D^{20}$ = +85° C. NMR 1H: 1.3(2H,m), 1.8(1H,m), 2.0(1H,m), 2.3(3H,s), 2.4(3H,s), 5.7(2H,m), 6.2(1H,d), 6.9-8.0(8H,m).

EXAMPLE L (±)-(2E,4E)-N-Phenyl-5-[c-2-(3,4-dibromophenyl)-r-1-fluorocyclopropyl]penta-2,4-dienthioamide (106)

The title compound was prepared from c-2-(3,4-dibromophenyl)-r-1-fluorocyclopropylmethanol (example B) in an analogous manner to that described in EP 0 369 762 Al (example 26) but using phenylisothiocyanate in place of isobutylisothiocyanate; m.pt.−68° C., m+1 480. NMR 1H: 1.5(1H,m), 1.8(1H,m), 2.3(1H,m), 6.0(1H,dd), 6.4(2H,m), 7.0-7.9(10H,m).

EXAMPLE M (2E,4E)-N-(2-Chlorophenyl)-12-(4-methyl-2-quinolinyloxy)-dodeca-2,4-dienamide (107)

Ethyl-12-(4-methyl-2-quinolinyloxy)dodeca-2,4-dionoate was prepared as described in EP 0 317 188 A2 example B. The above ester was converted to the title compound by analogy with example B(ii) and (iii). M+1 463. NMR 1H: 1.4(8H,m), 1.8(2H,m), 2.2(2H,m), 2.6(3H,s), 4.5(2H,m), 5.9(1H,d), 6.2(2H,m), 6.7-8.5(11H,m).

EXAMPLE N (2E/Z,4E)-N-(2-Chlorophenyl)-2-fluoro-3-methyl-12-(2-quinolinyloxy)dodeca-2,4-dienamide (108)

Ethyl 2-fluoro-3-methyl-12-(2-quinolinyloxy)dodeca-2,4-dienoate was prepared as described in EP 346 107 example 3. The above ester was converted to the title compound by analogy with example B(ii) and (iii). M+1 481. NMR 1H: 1.4(8H,m), 1.8(2H,m), 2.3(2M,m), 2.4(3H,s), 4.5(2H,m), 6.2(1H,m), 6.6(1H,d), 6.9-8.6(11H,m).

EXAMPLE O (2E,4E)-N-(2-Methylphenyl)-6-(5-trifluoromethyl-1,2,3,4-tetrahydro-2-naphthyl)hexa-2,4-dienamide (109)

6-(5-Trifluoromethyl-1,2,3,4-tetrahydronaphtha-2-yl)hexa-2,4-dienoic acid was prepared in an analogous manner to that described in EP 194 764 example 78. The above acid was converted to the title compound by analogy with example B(iii). M.pt.=171° C., NMR 1H: 1.4(2H,m), 1.9(2H,m), 2.3(3H,s), 2.5(2H,m), 3.1(1H,m), 5.9(1H,d), 6.2(2H,m), 6.9-7.9(9H,m).

EXAMPLE P (2E,4E)-N-(2-Methylphenyl)-6-(5-bromoindan-2-yl)hexa-2,4-dienamide (110)

6-(5-Bromoindan-2-yl)hexa-2,4-dienoic acid was prepared analogously to the method used in EP 194 764 example 79. The above acid was converted to the title compound by analogy with example B(iii). M.pt.−172° C., M+1 396. NMR 1H: 2.2(3H,s), 2.3(2H,m), 2.6(3H,m), 3.0(2H,m), 6.1(3H,m), 7.0(1H,d), 7.1-8.0(8H,m).

EXAMPLE Q (±)-(2E,4E)-N-Methyl-N-phenyl-5-[c-2-(3,4-dibromophenyl)-r-1-fluorocyclopropyl]penta-2,4-dienamide (111)

The above amide was prepared from N-methylaniline and (±)-(2E,4E)-5-[c-2-(3,4-dibromophenyl)-r-1-fluorocyclopropyl]penta-2,4-dienoic acid using the procedure described in example B(iii). The semi-solid had m+1 478. NMR 1H: 1.4(1H,m), 1.7(1H,m), 2.2(1H,m), 3.4(3H,s), 5.8(2H,m), 6.2(1H,m), 6.9-7.5(9H,m).

Compounds 112-119 were prepared in an analogous manner from the corresponding acids and amines.

N-Methylaniline was obtained from Aldrich Chemical Company. N-Methyl-o-toluidine was prepared according to literature methods (J.Chem.Soc. 1930, 992-4, Hickinbottom). The following compounds were similarly prepared: N-isopropyl-o-toluidine, N-isobutyl-o-toluidine, N-isopropylaniline and N-methyl-o-chloroaniline. N-Benzyl-o-toluidine was prepared according to Org.Syn. Col.Vol.1, 102.

EXAMPLE R (±)-(2E,4E)-N-(2-Methylphenyl)-N-carboethoxy-5-[c-2-(3,4-dibromophenyl)-r-1-fluorocyclopropyl]-penta-2,4-dienamide (120)

The acid chloride was prepared from dienoic acid (523 mg) according to example B dissolved in anhydrous THF (4 ml). N-Carboethoxytoluidine (240 mg) (prepared from o-toluidine and ethyl chloroformate) in THF (4 ml) was treated with n-butyl lithuim in hexane (0.838 ml at 1.6M) at −60° C. After 1 hour at −60° C. the above mentioned acid chloride was added and after a further hour at −50° C. the reaction worked-up in conventional fashion. Purification by chromatography gave the title compound as a glass like solid (300 mg). M.pt=40°-53° C., M+1 552. NMR 1H: 1.24(3H,t), 1.67,1.80(2H,2m), 2.22(3H,s), 2.33(1H,m), 4.25(2H,m), 6.01(1H,dofd), 6.68(1H,dofd), 6.96(1H,d), 7.1-7.7(8H,m).

| Compound No. | Compound Name |
|---|---|
| 1. | (±)-(2E,4E)-N-Phenyl-5-[c-2-(3,4-dibromophenyl)-r-1-fluorocyclopropyl]penta-2,4-dienamide |
| 2. | (±)-(2E,4E)-N-Phenyl-5-[c-2-(3,4-dibromophenyl)-r-1-fluorocyclopropyl]-3-methylpenta-2,4-dienamide |
| 3. | (±)-(2E,4E)-N-(2-Chlorophenyl)-5-[c-2-(3,4-dibromophenyl)-r-1-fluorocyclopropyl]penta-2,4-dienamide |
| 4. | (±)-(2E/Z,4E)-N-(2-Chlorophenyl)-5-[c-2-(3,4-dibromophenyl)-r-1-fluorocyclopropyl]-3-methylpenta-2,4-dienamide (2E:2Z = 7:3) |
| 5. | (±)-(2E,4E)-N-(4-Chlorophenyl)-5-[c-2-(3,4-dibromophenyl)-r-1-fluorocyclopropyl]-3-methylpenta-2,4-dienamide |
| 6. | (±)-(2E,4E)-N-(4-Fluorophenyl)-5-[c-2-(3,4-dibromophenyl)-r-1-fluorocyclopropyl]-3-methylpenta-2,4-dienamide |
| 7. | (±)-(2E/Z,4E)-N-(4-Fluorophenyl)-5-[c-2-(3,4-dibromophenyl)-r-1-fluorocyclopropyl]-3-methylpenta-2,4-dienamide (2E:2Z = 1:21) |
| 8. | (±)-(2E/Z,4E)-N-(2-Fluorophenyl)-5-[c-2-(3,4-dibromophenyl)-r-1-fluorocyclopropyl]-3-methylpenta-2,4-dienamide (2E:2Z = 6:4) |
| 9. | (±)-(2E,4E)-N-(3-Chlorophenyl)-5-[c-2-(3,4-dibromophenyl-r-1-fluorocyclopropyl]-3-methylpenta-2,4-dienamide |
| 10. | (±)-(2E,4E)-N-(2-Methoxyphenyl)-5-[c-2-(3,4-dibromophenyl)-r-1-fluorocyclopropyl]-3-methylpenta-2,4-dienamide |
| 11. | (±)-(2E,4E)-N-(2-Trifluoromethylphenyl)-5-[c-2-(3,4-dibromophenyl)-r-1-fluorocyclopropyl]-3-methylpenta-2,4-dienamide |
| 12. | (±)-(2E,4E)-N-(2-Fluorophenyl)-5-[c-2-(3,4-dibromophenyl)-r-1-fluorocyclopropyl]penta-2,4-dienamide |
| 13. | (±)-(2E/Z,4E)-N-(2-Methylphenyl)-5-[c-2-(3,4-dibromophenyl)-r-1-fluorocyclopropyl]-3-methylpenta-2,4-dienamide (2E:2E = 3:1) |
| 14. | (±)-(2E,4E)-N-(2-Methylphenyl)-5-[c-2-(3,4-dibromophenyl)-r-1-fluorocyclopropyl]-3-methylpenta-2,4-dienamide |
| 15. | (±)-(2E,4E)-N-(2,6-Dichlorophenyl)-5-[c-2-(3,4-dibromophenyl)-r-1-fluorocyclopropyl]penta-2,4-dienamide |
| 16. | (±)-(2E,4E)-N-(2,6-Difluorophenyl)-5-[c-2-(3,4-dibromophenyl)-r-1-fluorocyclopropyl]penta-2,4-dienamide |
| 17. | (±)-(2E,4E)-N-(2-Bromophenyl)-5-[c-2-(3,4-dibromophenyl)-r-1-fluorocyclopropyl]penta-2,4-dienamide |
| 18. | (±)-(2E,4E)-N-(2-Ethylphenyl)-5-[c-2-(3,4-dibromophenyl)-r-1-fluorocyclopropyl]penta-2,4-dienamide |
| 19. | (±) (2E,4E)-N-(2-Methylphenyl)-5-[c-2 (3,4-dibromophenyl)-r-1-fluorocyclopropyl]penta-2,4-dienamide |
| 20. | (±)-(2E,4E)-N-(2-Trifluoromethylphenyl)-5-[c-2-(3,4-dibromophenyl)-r-1-fluorocyclopropyl]penta-2,4-dienamide |
| 21. | (±)-(2E,4E)-N-(4-Fluorophenyl)-5-[c-2-(3,4-dibromophenyl)-r-1-fluorocyclopropyl]penta-2-4-dienamide |
| 22. | (±)-(2E,4E)-N-(3-Fluorophenyl)-5-[c-2-(3,4-dibromophenyl)-r-1-fluorocyclopropyl]penta-2,4-dienamide |
| 23. | (±)-(2E,4E)-N-(4-Methylphenyl)-5-[c-2-(3,4-dibroophenyl)-r-1-fluorocyclopropyl]-3-methylpenta-2,4-dienamide |
| 24. | (±)-(2E,4E)-N-(3-Methylphenyl)-5-[c-2-(3,4-dibromophenyl)-r-1-fluorocyclopropyl]-3-methylpenta-2,4-dienamide |
| 25. | (±)-(2E,4E)-N-(4-Methylphenyl)-5-[c-2-(3,4-dibromophenyl)-r-1-fluorocyclopropyl]penta-2,4-dienamide |
| 26. | (±)-(2E,4E)-N-(3-Methylphenyl)-5-[c-2-(3,4-dibromophenyl)-r-1-fluorocyclopropyl]penta-2,4-dienamide |
| 27. | (±)-(2E,4E)-N-(2-Fluoro-6-methylphenyl)-5-[c-2-(3,4-dibromophenyl)-r-1-fluorocyclopropyl]penta-2,4-dienamide |
| 28. | (±)-(2E,4E)-N-(2,6-Dimethylphenyl)-5-[c-2-(3,4-dibromophenyl)-r-1-fluorocyclopropyl]penta-2,4-dienamide |
| 29. | (±)-(2E,4E)-N-(4-Methoxyphenyl)-5-[c-2-(3,4-dibromophenyl)-r-1-fluorocyclopropyl]penta-2,4-dienamide |
| 30. | (±)-(2E,4E)-N-(2-Chloro-5-methylphenyl)-5-[c-2-(3,4-dibromophenyl)-r-1-fluorocyclopropyl]penta-2,4-dienamide |
| 31. | (±)-(2E,4E)-N-(4-Fluoro-2-methylphenyl)-5-[c-2-(3,4-dibromophenyl)-r-1-fluorocyclopropyl]penta-2,4-dienamide |
| 32. | (±)-(2E,4E)-N-(3-Fluoro-2-methylphenyl)-5-[c-2-(3,4-dibromophenyl)-r-1-fluorocyclopropyl]penta-2,4-dienamide |
| 33. | (±)-(2E,4E)-N-(3-Chloro-2-methylphenyl)-5-[c-2-(3,4-dibromophenyl)-r-1-fluorocyclopropyl]penta-2,4-dienamide |
| 34. | (±)-(2E,4E)-N-(2-Chloro-6-methylphenyl)-5-[c-2-(3,4-dibromophenyl)-r-1-fluorocyclopropyl]penta-2,4-dienamide |
| 35. | (±)-(2E,4E)-N-(2,3-Dichlorophenyl)-5-[c-2-(3,4-dibromophenyl)-r-1-fluorocyclopropyl]penta-2,4-dienamide |
| 36. | (±)-(2E,4E)(4-Trifluoromethylphenyl)-5-[c-2-(3,4-dibromophenyl)-r-1-fluorocyclopropyl]penta-2,4-dienamide |
| 37. | (±)-(2E,4E)-N-(3-Methoxyphenyl)-5-[c-2-(3,4-dibromophenyl)-r-1-fluorocyclopropyl]penta-2,4-dienamide |
| 38. | (±)-(2E,4E)-N-(2-5-Dimethylphenyl)-5-[c-2-(3,4-dibromophenyl)-r-1-fluorocyclopropyl]penta-2,4-dienamide |
| 39. | (±)-(2E,4E)-N-(2-Methylthiophenyl)-5-[c-2-(3,4-dibromophenyl)-r-1-fluorocyclopropyl]penta-2,4-dienamide |
| 40. | (±)-(2E,4E)-N-(2-Cyanophenyl) 5-[c-2-(3,4-dibromophenyl)-r-1-fluorocyclopropyl]penta-2,4-dienamide |
| 41. | (±)-(2E,4E)-N-(2-Isopropylphenyl)-5-[c-2-(3,4-dibromophenyl)-r-1-fluorocyclopropyl]penta-2,4-dienamide |
| 42. | (±)-(2E,4E)-N-(5-Chloro-2-methylphenyl)-5-[c-2-(3,4-dibromophenyl)-r-1-fluorocyclopropyl]penta-2,4-dienamide |
| 43. | (±)-(2E,4E)-N-(4-Fluoro-2-trifluoromethylphenyl)-5-[c-2-(3,4-dibromophenyl)-r-1-fluorocyclopropyl]penta-2,4-dienamide |
| 44. | (±)-(2E,4E)-N-(2-3-Dimethylphenyl)-5-[c-2-(3,4-dibromophenyl)-r-1-fluorocyclopropyl]penta-2,4-dienamide |
| 45. | (±)-(2E,4E)-N-(2-Nitrophenyl)-5-[c-2-(3,4-dibromophenyl)-r-1-fluorocyclopropyl]penta-2,4-dienamide |
| 46. | (±)-(2E,4E)-N-(5-Fluoro-2-methylphenyl)-5-[c-2-(3,4-dibromophenyl)-r-1-fluorocyclopropyl]penta-2,4-dienamide |
| 47. | (±)-(2E,4E)-N-(3-Bromo-2-methylphenyl)-5-[c-2-(3,4-dibromophenyl)-r-1-fluorocyclopropyl]penta-2,4-dienamide |
| 48. | (±)-(2E,4E)-N-(5-Iodo-2-methylphenyl)-5-[c-2-(3,4-dibromophenyl)-r-1-fluorocyclopropyl]penta-2,4-dienamide |
| 49. | (±)-(2E,4E)-N-(2-Phenoxyphenyl)-5-[c-2-(3,4-dibromophenyl)-r-1-fluorocyclopropyl]penta-2,4-dienamide |
| 50. | (±)-(2E,4E)-N-(2-Dimethylaminophenyl)-5[c-2-(3,4-dibromophenyl)-r-1-fluorocyclopropyl]penta-2,4-dienamide |
| 51. | (±)-(2E,4E)-N-(2-Ethoxycarbonyl)phenyl)-5-[c-2-(3,4-dibromophenyl)-r-1-fluorocyclopropyl]penta-2,4-dienamide |
| 52. | (±)-(2E,4E)-N-(2,4-Difluorophenyl)-5-[c-2-(3,4-dibromophenyl)-r-1-fluorocyclopropyl]penta-2,4-dienamide |
| 53. | (±)-(2E,4E)-N-(2-Acetylphenyl)-5-[c-2-(3,4-dibromophenyl)-r-1-fluorocyclopropyl]penta-2,4-dienamide |
| 54. | (±)-(2E,4E)-N-(2-Chloro-4-fluorophenyl)-5-[c-2-(3,4-dibromophenyl)-r-1-fluorocyclopropyl]penta-2,4-dienamide |
| 55. | (±)-(2E,4E)-N-[2-(1-Methylvinyl)phenyl]-5-[c-2-(3,4-dibromophenyl)-r-1-fluorocyclopropyl]penta-2,4-dienamide |
| 56. | (±)-(2E,4E)-N-(2-Iodophenyl)-5-[c-2-(3,4-dibromophenyl)-r-1-fluorocyclopropyl]penta-2,4-dienamide |
| 57. | (±)-(2E,4E)-N-(2-Ethynylphenyl)-5-[c-2-(3,4-dibromophenyl)-r-1-fluorocyclopropyl]penta-2,4-dienamide |
| 58. | (±)-(2E,4E)-N-(2-Formylphenyl)-5-[c-2-(3,4-dibromophenyl)-r-1-fluorocyclopropyl]penta-2,4-dienamide |
| 59. | (±)-(2E,4E)-N-(2-Trifluoromethoxyphenyl)-5-[c-2-(3,4-dibromophenyl)-r-1-fluorocyclopropyl]penta-2,4-dienamide |
| 60. | (±)-(2E,4E)-N-(2-Methoxycarbonyl)phenyl)-5-[c-2-(3,4-dibromophenyl)-r-1-fluorocyclopropyl]penta-2,4-dienamide |
| 61. | (±)-(2E,4E)-N-(2-Propylphenyl)-5-[c-2-(3,4-dibromophenyl)-r-1-fluorocyclopropyl]penta-2,4-dien- |
| 62. | (±)-(2E,4E)-N-(2-Fluorosulphonylphenyl)-5-[c-2-(3,4-dibromophenyl)-r-1-fluorocyclopropyl]penta-2,4-dienamide |
| 63. | (±)-(2E,4E)-N-(2-Chlorophenyl)-5-[c-2-(3,4-dibromophenyl)-r-1-fluorocyclopropyl]penta-2,4-dienamide |
| 64. | (±)-(2E,4E)-N-(2-Hydroxymethylphenyl)-5-[c-2-(3,4-dibromophenyl)-r-1-fluorocyclopropyl]penta-2,4-dienamide |
| 65. | (±)-(2E,4E)-N-(2-Aminophenyl)-5-[c-2-(3,4-dibromophenyl)-r-1-fluorocyclopropyl]penta-2,4-dien- |
| 66. | (±)-(2E,4E)-N-(2-Chlorophenyl)-5-[c-2-(3,4-dichlorophenyl)-r-1-fluorocyclopropyl]penta-2,4-dienamide |
| 67. | (±)-(2E/Z,4E)-N-(2-Chlorophenyl)-5-[c-2-(3,4-dichlorophenyl)-r-1-fluorocyclopropyl]-3-methylpenta-2,4-dienamide (2E:2Z = 5:4) |
| 68. | (±)-(2E,4E)-N-(2-Methylphenyl)-5-[c-2-(3,4-dichloro- |

-continued

| Compound No. | Compound Name |
|---|---|
| | phenyl)-r-1-fluorocyclopropyl]penta-2,4-dienamide |
| 69. | (±)-(2E,4E)-N-(2-Chlorophenyl)-5-[r-1-fluoro-c-2-(3,4,5-trichlorophenyl)cyclopropyl]penta-2,4-dienamide |
| 70. | (±)-(2E,4E)-N-(2-Methylphenyl)-5-[r-1-fluoro-c-2-(3,4,5-trichlorophenyl)cyclopropyl]penta-2,4-dienamide |
| 71. | (±)-(2E/Z,4E)-N-(2-Methylphenyl)-5-[c-2-(3,4-dichlorophenyl)-r-1-fluorocyclopropyl]-3-methylpenta-2,4-dienamide (2E:2Z = 1:1) |
| 72. | (±)-(2E,4E)-N-(2-Methylphenyl)-5-[r-1-fluoro-c-2-(4-iodophenyl)cyclopropyl]penta-2,4-dienamide |
| 73. | (±)-(2E,4E)-N-(2-Methylphenyl)-5-[c-2-(3-chloro-4-iodophenyl)-r-1-fluorocyclopropyl]penta-2,4-dienamide |
| 74. | (±)-(2E,4E)-N-(2-Methylphenyl)-5-[r-1-fluoro-c-2-(4-trifluoromethylphenyl)cyclopropyl]penta-2,4-dienamide |
| 75. | (±)-(2E,4E)-N-(2-Chlorophenyl)-5-[r-1-fluoro-c-2-(4-trifluoromethylphenyl)cyclopropyl]penta-2-4-dienamide |
| 76. | (±)-(2E,4E)-N-(2-Methylphenyl)-5-[r-1-fluoro-c-2-(4-trifluoromethylphenyl)cyclopropyl]-3-methylpenta-2,4-dienamide |
| 77. | (±)-(2E,4E)-N-(2-Methylphenyl)-5-[c-1-fluoro-N-(4-iodophenyl)cyclopropyl]-3-methylpenta-2,4-dienamide |
| 78. | (±)-(2E,4E)-N-(5-Fluoro-2-methylphenyl)-5-[c-2-(3,4-dichlorophenyl)-r-1-fluorocyclopropyl]penta-2,4 dienamide |
| 79. | (±)-(2E,4E)-N-(5-Fluoro-2-methylphenyl)-5-[r-1-fluoro-c-2-(3,4,5-trichlorophenyl)cyclopropyl]penta-2,4-dienamide |
| 80. | (±)-(2E,4E)-N-(2-Chloro-4-fluorophenyl)-5-[r-1-fluoro-c-2-(3,4,5-trichlorophenyl)cyclopropyl]penta-2,4-dienamide |
| 81. | (±)-(2E,4E)-N-(4-Fluoro-2-methylphenyl)-5-[r-1-fluoro-c-2-(3,4,5-trichlorophenyl)cyclopropyl]penta-2,4-dienamide |
| 82. | (±)-(2E,4E)-N-(4-Fluoro-2-methylphenyl)-5-[c-2-(3,4-dichlorophenyl)-r-1-fluorocyclopropyl]penta-2,4-dienamide |
| 83. | (=)-(2E,4E)-N-(2-Chloro-4-fluorophenyl)-5-[c-2-(3,4-dichlorophenyl)-r-1-fluorocyclopropyl]penta-2,4-dienamide |
| 84. | (±)-(2E,4E)-N-(2-Methylphenyl)-5-[c-2-(4-bromophenyl)-r-1-fluorocyclopropyl]penta-2,4-dienamide |
| 85. | (±)-(2E,4E)-N-(2-Chlorophenyl)-5-[c-2-(4-bromophenyl)-r-1-fluorocyclopropyl]penta-2-4-dienamide |
| 86. | (±)-(2E,4E)-N-(2-fluoromethylphenyl)-5-[c-2-(3,4-dibromophenyl)-r-1-fluorocyclopropyl]penta-2,4-dienamide |
| 87. | (±)-(2E,4E)-N-(2-Hydroxyphenyl)-5-[c-2-(3,4-dibromophenyl)-r-1-fluorocyclopropyl]penta-2,4-dienamide |
| 88. | (+)-(2E,4E)-N-(2-Methylphenyl)-5 [(1 S,2 R)-2-(3,4-dibromophenyl)-1-fluorocyclopropyl]penta-2,4-dienamide |
| 89. | (−)-(2E,4E)-N-(2-Methylphenyl)-5-[(1 S,2 R)-2-(3,4-dibromophenyl)-1-fluorocyclopropyl]penta-2,4-dienamide |
| 90. | (±)-(2E,4E)-N-(2-Methylphenyl)-5-[r-1-chloro-c-(3,4-dichlorophenyl)-cyclopropyl]-3-methylpenta-2,4-dienamide |
| 91. | (±)-(2E,4E)-N-(2-Chlorophenyl)-5-[r-1-chloro-c-2-(3,4-dibromophenyl)cyclopropyl]penta-2,4-dienamide |
| 92. | (±)-(2E,4E)-N-(2-Methylphenyl)-5-[r-1-chloro-c-2-(3,4-dibromophenyl)cyclopropyl]penta-2,4-dienamide |
| 93. | (±)-(2E,4E)-N-(2-Methylphenyl)-5-[r-1-chloro-c-2-(3,4-dibromophenyl)cyclopropyl)-3-methylpenta-2,4 dienamide |
| 94. | (±)-(2E/Z,4E)-N-(2-Methylphenyl)-5-[r-1-chloro-c-2-(3,4-dibromophenyl)cyclopropyl)-3-methylpenta-2,4-dienamide |
| 95. | (±)-(2E/Z,4E)-N-(2-Chlorophenyl)-5-[r-1-chloro-c-(3,4-dibromophenyl)cyclopropyl]-3-methylpenta-2,4-dienamide (2E:2E = 2:1) |
| 96. | (±)-(2Z,4E)-N-(2-Methylphenyl)-5-[c-2-(3,4-dibromophenyl)-r-1-fluorocyclopropyl]-2 fluoro-3-methylpenta-2,4-dienamide |
| 97. | (±)(2Z,4E)-N-(2-Chlorophenyl)-5-[c-2-(3,4-dibromophenyl)-r-1-fluorocyclopropyl]-2-fluoro-3-methylpenta-2,4-dienamide |
| 98. | (±)-(2Z,4E)-N-(2-Methylphenyl)-5-[c-2-(3,4-dichlorophenyl)-r-1-fluorocyclopropyl]-2-fluoropenta-2,4-dienamide |
| 99. | (±)-(2Z,4E)-N-(2-Chlorophenyl)-5-[c-2-(3,4-dichlorophenyl)-±-1-fluorocyclopropyl]-2-fluoropenta-2,4-dienamide |
| 100. | (±)-(2Z,4E)-N-(2-Chlorophenyl)-5-[c-2-(3,4-dibromophenyl)-r-1-fluorocyclopropyl]-2-fluoropenta-2,4-dienamide |
| 101. | (±)-(2E,4E)-N-(2-Methylphenyl)-5-[c-2-(3,4-dibromophenyl)-r-1-fluorocyclopropyl]-2-fluoropenta-2,4-dienamide |

-continued

| Compound No. | Compound Name |
|---|---|
| 102. | (±)-(2E,4E)-N-(2-Methylphenyl)-5-[trans-2-(3,4-dibromophenyl)cyclopropyl]-3-methylpenta-2,4-dienamide |
| 103. | (±)-(2E,4E)-N-(2-Methylphenyl)-5-[trans-2-(3,4-dibromophenyl)cyclopropyl]penta-2,4-dienamide |
| 104. | (−)-(2E,4E)-N-(2-Methylphenyl)-5-[(1 R,2 S)-trans-2-(3,4-dibromophenyl)cyclopropyl]-3-methylpenta-2,4-dienamide |
| 105. | (+)-(2E,4E)-N-(2-Methylphenyl)-5-[(1 S,2 R)-trans-2-(3,4-dibromophenyl)cyclopropyl]-3-methylpenta-2,4-dienamide |
| 106. | (±)-(2E,4E)-N-Phenyl-5-[c-2-(3,4-dibromophenyl)-r-1-fluorocyclopropyl]penta-2,4-dienthioamide |
| 107. | (2E,4E)-N-(2-Chlorophenyl)-12-(4-methyl-2-quinolinyloxy)-dodeca-2,4-dienamide |
| 108. | (2E/Z,4E)-N-(2-Chlorophenyl)-2-fluoro-3-methyl-12-(2-quinolinyloxy)-dodeca-2,4-dienamide |
| 109. | (2E,4E)-N-(2-Methylphenyl)-6-(5-trifluoromethyl-1,2,3,4-tetrahydro-2-naphthyl)hexa-2,4-dienamide |
| 110. | (2E,4E)-N-(2-Methylphenyl)-6-(5-bromoindan-2-yl)hexa-2,4-dienamide) |
| 111. | (±)-(2E,4E)-N-Methyl-N-phenyl-5-[c-2-(3,4-dibromophenyl)-r-1-fluorocyclopropyl]penta-2,4-dienamide |
| 112. | (±)-(2E,4E)-N-Isopropyl-N-Isopropyl-N-(2-methylphenyl)-5-[c-2-(3,4-dibromophenyl)-r-1-fluorocyclopropyl]penta-2,4-dienamide |
| 113. | (±)-(2E,4E)-N-Isobutyl-N-(2-Methylphenyl)-5-[c-2-(3,4-dibromophenyl)--1-fluorocyclopropyl]penta-2,4-dienamide |
| 114. | (±)-(2E,4E)-N-Isopropyl-N-phenyl-5-[c-2-(3,4-dibromophenyl)-r-1-fluorocyclopropyl]penta-2,4-dienamide |
| 115. | (±)-(2E,4E)-N-Methyl-N-(2-methylphenyl)-5-[c-2-(3,4-dibromophenyl)-r-1-fluorocyclopropyl]-3-methylpenta-2,4-dienamide |
| 116. | (±)-(2E,4E)-N-Methyl-N-(2-methylphenyl)-5-[c-2-(3,4-dibromophenyl)-r-1-fluorocyclopropyl]penta-2,4-dienamide |
| 117. | (±)-(2E,4E)-N-Benzyl-N-(2-methylphenyl)-5-[c-2-(3,4-dibromophenyl)-r-1-fluorocyclopropyl]penta-2,4-dienamide |
| 118. | (±)-(2E,4E)-N-(2-Chlorophenyl)-N-methyl-5-[c-2-(3,4-dibromophenyl)-r-1-fluorocyclopropyl]penta-2,4,dienamide |
| 119. | (±)-(2E,4E)-N-(2-Chlorophenyl)-N-methyl-5-[c-2-(3,4-dibromophenyl)-r-1-fluorocyclopropyl]-3-methylpenta-2,4-dienamide |
| 120. | (±)-(2E,4E)-N-(2-Methylphenyl)-N-carboethoxy-5-[c-2-(3,4-dibromophenyl)-r-1-fluorocyclopropyl]-penta-2,4-dienamide |

TABLE 1

| Compound No. | Wittig Reagent | Aniline | E,E:E,Z a:b |
|---|---|---|---|
| 1 | 1 | Aniline | a |
| 2 | 2 | Aniline | a |
| 3 | 1 | 2-Chloroaniline | a |
| 4 | 2 | 2-Chloroaniline | 7:3 |
| 5 | 2 | 4-Chloroaniline | a |
| 6 | 2 | 4-Fluoroaniline | a |
| 7 | 2 | 4-Fluoroaniline | 95:5 |
| 8 | 2 | 2-Fluoroaniline | 6:4 |
| 9 | 2 | 3-Chloroaniline | a |
| 10 | 2 | 2-Methoxyaniline | a |
| 11 | 2 | 2-Trifluoromethylaniline | a |
| 12 | 1 | 2-Fluroaniline | a |
| 13 | 2 | 2-Methylaniline | 3:1 |
| 14 | 2 | 2-Methylaniline | a |
| 15 | 1 | 2,6-Dichloroaniline | a |
| 16 | 1 | 2,6-Difluoroaniline | a |
| 17 | 1 | 2-Bromoaniline | a |
| 18 | 1 | 2-Ethylaniline | a |
| 19 | 1 | 2-Methylaniline | a |
| 20 | 1 | 2-Trifluoromethylaniline | a |
| 21 | 1 | 4-Fluroaniline | a |
| 22 | 1 | 3-fluoroaniline | a |
| 23 | 2 | 4-Methylaniline | a |
| 24 | 2 | 3-Methylaniline | a |
| 25 | 1 | 4-Methylaniline | a |

TABLE 1-continued

| Compound No. | Wittig Reagent | Aniline | E,E:E,Z a:b |
|---|---|---|---|
| 26 | 1 | 3-Methylaniline | a |
| 27 | 1 | 2-Fluoro-6-methylaniline | a |
| 28 | 1 | 2,6-Dimethylaniline | a |
| 29 | 1 | 4 Methoxyaniline | a |
| 30 | 1 | 2-Chloro-5-methylaniline | a |
| 31 | 1 | 4-Fluoro-2-methylaniline | a |
| 32 | 1 | 3-Fluoro-2-methylaniline | a |
| 33 | 1 | 3-Chloro-2-methylaniline | a |
| 34 | 1 | 2-Chloro-6-methylaniline | a |
| 35 | 1 | 2,3-Dichloroaniline | a |
| 36 | 1 | 4-Trifluoromethylaniline | a |
| 37 | 1 | 3-Methoxyaniline | a |
| 38 | 1 | 2,5-Dimethylaniline | a |
| 39 | 1 | 2-Methylthioaniline | a |
| 40 | 1 | 2-Cyanoaniline | a |
| 41 | 1 | 2-Isopropylaniline | a |
| 42 | 1 | 5-Chloro-2-methylaniline | a |
| 43 | 1 | 4-Fluoro-2-trifluoromethyl aniline | a |
| 44 | 1 | 2,3-Dimethylaniline | a |
| 45 | 1 | 2-Nitroaniline | a |
| 46 | 1 | 3-Fluoro-6-methylaniline | a |
| 47 | 1 | 3-Bromo-2-methylaniline | a |
| 48 | 1 | 3-Iodo-6-methylaniline | a |
| 49 | 1 | 2-Phenoxyaniline | a |
| 50 | 1 | 2-N,N-Dimethylaminoaniline | a |
| 51 | 1 | 2-Ethoxycarbonylaniline | a |
| 52 | 1 | 2,4-Difluoroaniline | a |
| 53 | 1 | 2-Acetylaniline | a |
| 54 | 1 | 2-Chloro-4-fluoroaniline | a |
| 55 | 1 | 2-Isopropenylaniline | a |
| 56 | 1 | 2-Iodoaniline | a |
| 57 | 1 | 2-Ethynylaniline * | a |
| 58 | 1 | 2-Formylaniline | a |
| 59 | 1 | 2-Trifluoromethoxyaniline | a |
| 60 | 1 | 2-Methoxycarbonylaniline | a |
| 61 | 1 | 2-n-Propylaniline | a |
| 62 | 1 | 2-Fluorosulphonylaniline | a |
| 63 | 2 | 2-Chloroaniline | a |
| 64 | 1 | 2-Hydroxymethylaniline | a |
| 65 | 1 | 1,2-Phenylenediamine | a |

* 2-Ethynylaniline was prepared according to Arcadi et al., Tet. Letts. 30(19), 2581, 1989

Wittig Reagent
1 = triethyl 4-phosphonocrotonate
2 = triethyl 3-methyl-4-phosphonocrotonate

TABLE 2

| Compound No. | Wittig Reagent | Benzaldehyde where R is | Aniline | E,E:E,Z a:b |
|---|---|---|---|---|
| 66 | 1 | 3,4-Dichloro | 2-chloroaniline | a |
| 67 | 2 | 3,4-Dichloro | 2-chloroaniline | 5:4 |
| 68 | 1 | 3,4-Dichloro | 2-methylaniline | a |
| 69 | 1 | 3,4,5-Trichloro | 2-chloroaniline | a |
| 70 | 1 | 3,4,5-Trichloro | 2-methylaniline | a |
| 71 | 2 | 3,4-Dichloro | 2-methylaniline | 1:1 |
| 72 | 1 | 4-Iodo | 2-methylaniline | a |
| 73 | 1 | 3-Chloro-4-iodo | 2-methylaniline | a |
| 74 | 1 | 4-Trifluoromethyl | 2-methylaniline | a |
| 75 | 1 | 4-Trifluoromethyl | 2-chloroaniline | a |
| 76 | 2 | 4-Trifluoromethyl | 2-methylaniline | a |
| 77 | 2 | 4-Iodo | 2-methylaniline | a |
| 78 | 1 | 3,4-Dichloro | 4-fluoro-2-methyl-aniline | a |
| 79 | 1 | 3,4,5-Trichloro | 4-fluoro-2-methyl-aniline | a |
| 80 | 1 | 3,4,5-Trichloro | 2-chloro 4-fluoro-aniline | a |
| 81 | 1 | 3,4,5-Trichloro | 4-fluoro-2-methyl-aniline | a |
| 82 | 1 | 3,4-Dichloro | 4-fluoro-2-methyl-aniline | a |
| 83 | 1 | 3,4-Dichloro | 2-chloro-4-fluoro-aniline | a |
| 84 | 1 | 4-Bromo | 2-methylaniline | a |
| 85 | 1 | 4-Bromo | 2-chloroaniline | a |
| 86–90 | See experimental section | | | |
| 91 | 1 | 3,4-Dibromo | 2-chloroaniline | a |
| 92 | 1 | 3,4-Dibromo | 2-methylaniline | a |
| 93 | 2 | 3,4-Dibromo | 2-methylaniline | a |
| 94 | 2 | 3,4-Dibromo | 2-methylaniline | 2:1 |
| 95 | 2 | 3,4-Dibromo | 2-chloroaniline | 2:1 |
| 96–98 | See experimental section | | | |
| 99 | 3 | 3,4-Dichloro | 2-chloroaniline | a |
| 100 | 3 | 3,4-Dibromo | 2-methylaniline | a |
| 101 | 3 | 3,4-Dibromo | 2-chloroaniline | a |
| 102–110 | See experimental section | | | |
| 111 | 1 | 3,4-Dibromo | N-methylaniline | a |
| 112 | 1 | 3,4-Dibromo | N-isopropyl-o-toluidine | a |
| 113 | 1 | 3,4-Dibromo | N-isobutylaniline | a |
| 114 | 1 | 3,4-Dibromo | N-isopropylaniline | a |
| 115 | 2 | 3,4-Dibromo | N-methyl-o-toluidine | a |
| 116 | 1 | 3,4-Dibromo | N-methyl-o-toluidine | a |
| 117 | 1 | 3,4-Dibromo | N-benzyl-o-toluidine | a |
| 118 | 1 | 3,4-Dibromo | N-methyl-o-chloroaniline | a |
| 119 | 2 | 3,4-Dibromo | N-methyl-o-chloroaniline | a |

Wittig Reagent
1 = triethyl 4-phosphonocrotonate
2 = triethyl 3-methyl-4-phosphonocrotonate
3 = triethyl 2-fluoro-4-phosphocrotonate

BIOLOGICAL DATA

The following examples illustrate, in a non-limiting manner, the pesticidal activity of compounds of formula (I):

EXAMPLE A—SPRAY TESTR

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

Musca domestica 20 female Musca were contained in a cardboard cylinder with gauze over both ends. Solution containing the compound was sprayed onto the insects so enclosed and mortality assessed after 48 hours at 25° C.

The following compounds were active at 1000 ppm or less
5, 7, 9

The following compounds were active at 200 ppm or less:
1, 2, 3, 4, 6, 8

Plutella xylostella

Chinese cabbage leaf discs infested with 8 2nd instar Plutella larvae were sprayed with the solution containing the compound. Mortality was assessed after 2 days at 25° C.

The following compounds were active at 1000 ppm or less:
5, 7, 9, 10, 14, 17, 20, 21, 22, 98, 50, 55, 57, 81, 83, 100, 114

The following compounds were active at 200 ppm or less:
1, 2, 3, 4, 6, 8, 11, 12, 13, 16, 19, 88, 89, 90, 93, 94, 95, 99, 101, 28, 66, 96, 97, 31, 52, 54, 58, 63, 65, 66, 68, 70, 74, 75, 76, 77, 78, 79, 80, 82, 84, 85, 111–119 except 114, 117

Tetranychus urticae

Leaf discs of infested french bean were sprayed with the solution containing the compound. Mortality was assessed after 2 days at 25° C.

The following compounds were active at 1000 ppm or less
6, 14, 16, 20, 28, 71, 96

Spodoptera littoralis

Uninfested leaves were sprayed with the test solution containing the compound and left to dry. These were then infested with 10 newly hatched larvae. Mortality was assessed after 3 days.

The following compounds were active at 1000 ppm or less:
5, 7, 9, 10, 14, 22, 98, 32, 39, 45, 53, 55, 62, 75, 81, 83, 114

The following compounds were active at 200 ppm or less:
1, 2, 3, 4, 6, 8, 11, 12, 13, 16, 17, 19, 20, 21, 28, 66, 96, 97, 31, 34, 44, 46, 50, 52, 54, 58, 63, 64, 66, 67, 68, 69, 70, 71, 72, 73, 74, 76, 77, 78, 79, 82, 84, 85, 86, 88, 89, 90, 91, 92, 93, 94, 95, 99, 100, 101, 111–119 except 114.

Myzus persicae 10 adult Myzus were placed on a leaf disc of chinese cabbage. 24 hours later the disc was sprayed with the solution containing the compound. Mortality was assessed after 2 days at 25° C.

The following compounds were active at 1000 ppm or less
2, 4, 6, 8, 14, 13, 44, 68, 97, 115

The following compounds were active at 200 ppm or less
11, 71, 67, 96

Diabrotica undecimpunctata

A filler paper and a piece of artificial diet were sprayed with the solution containing the compound. These were then infested with 2nd instar larvae and held for 48 hours, at which point mortality was assessed.

The following compounds were active at 1000 ppm or less:
2, 3, 6, 9, 14, 16, 19, 20, 28, 98, 31, 44, 49, 54, 58, 61, 66, 67, 69, 74, 75, 79, 82, 85, 93, 94, 99, 101, 112, 115, 116

The following compounds were active at 200 ppm or less:
4, 11, 13, 96, 97, 46, 68, 71, 72, 73, 77, 84, 89, 92

EXAMPLE B—TOPICAL APPLICATION TESTS

Blattella germanica 0.5 μl of a solution of the compound in butanone (with or without piperonyl butoxide) was topically applied to male B.germanica. Mortality was assessed after 6 days.

The following compounds were active at 10 μg or less (+piperonyl butoxide)
2, 4, 6, 8, 11, 13, 14, 96, 97, 58, 63, 67, 71, 76, 77, 84, 89, 93, 94, 99, 100, 111, 115, 119

Musca domestica

Female houseflies (in batches of 20) were treated with 0.3 μl of solutions of the compound and piperonyl butoxide in butanone. Mortality was assessed after two days.

The following compounds were active at 1.5 μg or less (+piperonyl butoxide)
98, 34, 39, 54, 55, 74, 75, 83, 88, 99, 100, 113, 118, 119

The following compounds were active at 0.3mg or less (+piperonyl butoxide)
1, 2, 3, 4, 6, 8, 9, 11, 12, 13, 14, 17, 18, 19, 21, 22, 23, 24, 28, 66, 96, 97, 31, 32, 38, 46, 50, 52, 63, 66, 67, 68, 69, 70, 71, 72, 73, 76, 77, 78, 79, 81, 82, 84, 85, 86, 89, 90, 91, 92, 93, 94, 95, 101, 111, 112, 115, 116, 117

The following compounds were active at 10 μg or less (+piperonyl butoxide)
2, 4, 6, 8, 11, 13, 14

Musca domestica

Female houseflies (in batches of 20) were treated with 0.3 μl of solutions of the compound and piperonyl butoxide in butanone. Mortality was assessed after two days.

1, 2, 3, 4, 6, 8, 9, 11, 12, 13, 14, 17, 18, 19, 21, 22, 23, 24

TABLE 3

Physico-chemical data

| Compound No. | m.pt. °C. | Mass Spectrum M+1 |
|---|---|---|
| 1 | 174-5 | 464 |
| 2 | 138 | 478 |
| 3 | 168-9 | 498 |
| 4 | 60 | 512 |
| 5 | 147 | 512 |
| 6 | 127 | 498 |
| 7 | 64 | 498 |
| 8 | 60 | 496 |
| 9 | 148 | 512 |
| 10 | 104 | 508 |
| 11 | 49 | 546 |
| 12 | 171-6 | 482 |
| 13 | 132 | 492 |
| 14 | 144 | 492 |
| 15 | 199 | 532 |
| 16 | 189 | 500 |
| 17 | 177 | 542 |
| 18 | 193 | 492 |
| 19 | 186 | 478 |
| 20 | 188 | 532 |
| 21 | 181 | 482 |
| 22 | 189 | 482 |
| 23 | 154 | 492 |
| 24 | 127 | 492 |
| 25 | 189 | — |
| 26 | 182 | 478 |
| 27 | 193.5 | 496 |
| 28 | 185.6 | 492 |
| 29 | 206.2 | 494 |
| 30 | 194.5 | 512 |
| 31 | 192.2 | 496 |
| 32 | 192.1 | 496 |
| 33 | 193.9 | 512 |
| 34 | 188 | 512 |
| 35 | 169.4 | 532 |
| 36 | 194.1 | 532 |
| 37 | 155.4 | 494 |
| 38 | 192.8 | 492 |
| 39 | 156.1 | 510 |
| 40 | 179.3 | 489 |
| 41 | 178 | 506 |
| 42 | 197.5 | 512 |
| 43 | 165.9 | 550 |
| 44 | 192.5 | 492 |
| 45 | 157.4 | 509 |
| 46 | 180.3 | 496 |
| 47 | 271.6 | 556 |
| 48 | 191.3 | 604 |
| 49 | 153 | 556 |
| 50 | 133 | 507 |
| 51 | 131.6 | 536 |
| 52 | 179 | 500 |
| 53 | 149.7 | 506 |
| 54 | 176.6 | 518 |
| 55 | 226.3 | 504 |
| 56 | 192.5 | 590 |
| 57 | 178.1 | 488 |
| 58 | 141.5 | 492 |
| 59 | 182.7 | 548 |
| 60 | 156 | 522 |
| 61 | 183.2 | 506 |
| 62 | >300 | 546 |
| 63 | 102.7 | 512 |
| 64 | 183.9 | 494 |
| 65 | 165 | 479 |
| 66 | 166-7 | 410 |
| 67 | 45-6 | 424 |
| 68 | 185-6 | 390 |
| 69 | 176-7 | 444 |
| 70 | 192-3 | 424 |
| 71 | 127-8 | 404 |
| 72 | 183 | 448 |
| 73 | 189 | 482 |
| 74 | 193 | — |
| 75 | 171 | — |
| 76 | 140 | — |
| 77 | 139 | — |
| 78 | 182.5 | 408 |
| 79 | 185.1 | 442 |
| 80 | 186.1 | 462 |
| 81 | 186.8 | 442 |
| 82 | 183.3 | 408 |
| 83 | 178.5 | 428 |
| 84 | 165.6 | 400 |
| 85 | 139-44 | 420 |
| 86 | 163-5 | 566 |
| 87 | 167.7 | 482 |
| 88 | 185-6 | — |
| 89 | 174.6 | — |
| 90 | 170.6 | — |
| 91 | 140-1 | 514 |
| 92 | 170-1 | 494 |
| 93 | 153-4 | 508 |
| 94 | 140-1 | 508 |
| 95 | 142-3 | 528 |
| 96 | 104-5 | 510 |
| 97 | 128-9 | 530 |
| 98 | 152-3 | 408 |
| 99 | 109-10 | 428 |
| 100 | 154-5 | 496 |
| 101 | 111-2 | 516 |
| 102-111, | See experimental section | |
| 112 | 129-30 | 520 |
| 113 | oil | 534 |
| 114 | 135-7 | 506 |
| 115 | 135 | 492 |
| 116 | oil | 506 |
| 117 | 51-3 | 568 |
| 118 | 126-8 | 512 |
| 119 | oil | 526 |

TABLE 4

| Compound No. | $^1$NMR Data |
|---|---|
| 1. | 1.7(1H, m), 2.1(1H, m), 2.6(1H, m), 6.2-6.6(3H, m), 7.1(1H, m), 7.2-7.0(8H, m), 10.1(1H, s). |
| 2. | 1.5(1H, m), 1.8(1H, m), 2.3(1H, m), 2.4(3H, s), 5.9(2H, m), 6.4(1H, d), 7-7.9(9H, m). |
| 3. | 1.6(1H, m), 1.8(1H, m), 2.3(1H, m), 5.9(1H, dd), 6.1(1H, d), 6.5(1H, dd), 7.4(1H, dd), 7-8.5(8H, m). |
| 4. | 1.7(2H, m), 2.1 and 2.4(3H, s), 2.3(1H, m), 5.9-6.1(3H, m), 6.5 and 7.9(1H, d), 7.8.5(7H, m). |
| 5. | 1.5(1H, m), 1.8(1H, m), 2.3(1H, m), 2.4(3H, s), 5.9(2H, m), 6.4(1H, d), 7.1(1H, dd), 7.2-7.6(7H, m). |
| 6. | 1.5(1H, m), 1.8(1H, m), 2.3(1H, m), 2.4(3H, s), 5.9(2H, m), 6.4(1H, d), 7-7.6(8H, m). |
| 7. | 1.4-1.8(2H, m), 1.9(3H, s), 2.2(1H, m), 5.7(1H, s), 6.0(1H, dd), 6.9-8(9H, m). |
| 8. | 1.5-1.9(2H, m), 2.1 and 2.4(3H, s), 2.3(1H, m), 5.8-6.2(3H, m), 6.4 and 7.9(1H, d), 7-8.5(7H, m). |

TABLE 4-continued

| Compound No. | ¹NMR Data |
|---|---|
| 9. | 1.5(1H, m), 1.8(1H, m), 2.3(1H, m), 2.4(3H, s), 5.9(2H, m), 6.4(1H, d), 7-7.8(8H, m). |
| 10. | 1.5(1H, m), 1.8(1H, m), 2.3(1H, m), 2.4(3H, s), 3.9(3H, s), 5.9(2H, m), 6.4(1H, d), 6.9-7.6(6H, m), 7.9(1H, s), 8.5(1H, d). |
| 11. | 1.6(1H, m), 1.8(1H, m), 2.3(1H, m), 2.4(3H, s), 5.9(2H, m), 6.4(1H, d), 7-8.4(8H, m). |
| 12. | 1.3(1H, m), 1.5(1H, m), 2.0(1H, m), 5.6(1H, dd), 6.1(2H, m), 7.0(1H, dd), 6.7-7.3(6H, m), 7.9(1H, m), 9.0(1H, s). |
| 13. | 1.6(1H, m), 1.8(1H, m), 2.1 and 2.4(3H, s), 2.25(3H, s), 2.3(1H, m), 5.8-6.5(3H, m), 6.9-8(8H, m). |
| 14. | 1.6(1H, m), 1.8(1H, m), 2.25(3H, s), 2.3(1H, m), 2.4(3H, s), 5.9(2H, m), 6.4(1H, d), 6.9-8(8H, m). |
| 15. | 1.75(1H, m), 2.2(1H, m), 2.7(1H, m), 6.4(2H, m), 6.6(1H, m), 7.2-7.9(7H, m), 10.1(1H, s). |
| 16. | 1.1(1H, m), 1.6(1H, m), 1.8(1H, m), 6.0(1H, dd), 6.2-6.5(2H, m), 6.9-7.9(7H, m), 9.6(1H, s). |
| 17. | 1.05(1H, m), 1.25(1H, m), 1.8(1H, m), 5.3-5.5(1H, m), 5.7-6(2H, m), 6.4-7.4(8H, m), 8.5(1H, s). |
| 18. | 1.1(3H, t), 1.6(1H, m), 1.75(1H, m), 2.4-2.7(3H, m), 6.0(1H, dd), 6.2-6.5(2H, m), 7-9.3(9H, m). |
| 19. | 1.8(1H, m), 2.2(1H, m), 2.3(3H, s), 2.7(1H, m), 6.2-6.6(3H, m), 7.1-7.4(5H, m), 7.6(1H, d), 7.8(2H, m), 9.5(1H, s). |
| 20. | 1.8(1H, m), 2.2(1H, m), 2.7(1H, m), 6.3-6.7(3H, m), 7.3(2H, dd), 7.5-7.9(6H, m), 9.8(1H, s). |
| 21. | 1.45(1H, m), 1.85(1H, m), 2.4(1H, m), 5.9-6.4(3H, m), 6.9-7.2(4H, m), 7.4-7.6(4H, m), 9.7(1H, s). |
| 22. | 1.5(1H, m), 1.9(1H, m), 2.4(1H, m), 6.0-6.4(3H, m), 6.7(1H, m), 7-7.6(7H, m), 9.5(1H, s). |
| 23. | 1.6(1H, m), 1.8(1H, m), 2.3(1H, m) 2.35(3H, s), 2.4(3H, s), 5.9(2H, m), 6.4(1H, d), 7-7.6(8H, m). |
| 24. | 1.5(1H, m), 1.9(1H, m), 2.1(3H, s), 2.15(3H, s), 2.4(1H, m), 5.7-6.2(3H, m), 6.65(1H, d), 6.9-7.5(6H, m), 9.75(1H, s). |
| 25. | 1.45(1H, m), 1.75(1H, m), 2.05(3H, s), 2.4(1H, m), 5.9-6.3(3H, m), 6.8-7.5(8H, m), 9.85(1H, s). |
| 26. | 1.65(1H, m), 2.1(1H, m), 2.25(3H, s), 2.65(1H, m), 6.2-6.4(2H, m), 6.5(1H, dd), 6.9(1H, d), 7.1-7.8(7H, m), 10.05(1H, S). |
| 27. | 1.6(1H, m), 2.05(1H, m), 2.1(3H, s), 2.6(1H, m), 6.1-6.5(3H, m), 7.0(1H, m), 7.15-7.75(6H, m), 9.6(1H, s). |
| 28. | 1.65(1H, m), 2.05(1H, m), 2.1(6H, s), 2.6(1H, m), 6.1-6.55(3H, m), 7-7.7(7H, m), 9.4(1H, s). |
| 29. | 1.45(1H, m), 1.9(1H, m), 2.4(1H, m), 3.5(3H, s), 5.9-6.3(3H, m), 6.6-7.5(8H, m), 9.8(1H, s). |
| 30. | 1.4(1H, m), 1.9(1H, m), 2.1(3H, s), 2.4(1H, m), 6-6.3(3H, m), 6.75-7.5(7H, m), 9.4(1H, s). |
| 31. | 1.55(1H, m), 1.8(1H, m), 2.15(3H, s), 2.45(1H, m), 5.9-6.4(3H, m), 6.7-7.5(7H, m), 9.2(1H, s). |
| 32. | 1.55(1H, m), 2.0(1H, m), 2.1(3H, s), 2.6(1H, m), 6.1-6.55(3H, m), 6.9-7.7(7H, m), 9.55(1H, m). |
| 33. | 1.65(1H, m), 2.05(1H, m), 2.2(3H, s), 2.6(1H, m), 6.1-6.5(3H, m), 7.1-7.7(7H, m), 9.6(1H, s). |
| 34. | 1.6(1H, m), 2.0(1H, m), 2.15(3H, s), 2.55(1H, m), 6.1-6.55(3H, m), 7.1-7.7(7H, m), 9.6(1H, s). |
| 35. | 1.65(1H, m), 2.05(1H, m), 2.6(1H, m), 6.1-6.5(3H, m), 7.1-7.8(7H, m), 9.7(1H, s). |
| 36. | 1.2(1H, m), 1.8(1H, m), 2.3(1H, m), 5.8-6.1(3H, m), 6.5(1H, dd), 7-7.8(8H, m). |
| 37. | 1.65(1H, m), 2.05(1H, m), 2.6(1H, m), 3.2(3H, s), 6.1-6.5(3H, m), 6.6(1H, dd), 7.1-7.7(7H, m), 10(1H, s). |
| 38. | 1.7(1H, m), 2.05(1H, m), 2.2(3H, s), 2.3(3H, s), 2.6(1H, m), 6.1-6.5(3H, m), 6.8.7.7(7H, m), 9.3(1H, s). |
| 39. | 1.65(1H, m), 2.0(1H, m), 2.4(3H, s), 2.6(1H, m), 6.1-6.5(3H, m), 7.1-7.7(8H, m), 9.4(1H, s). |
| 40. | 1.7(1H, m), 2.1(1H, m), 2.6(1H, m), 6.2-6.6(3H, m), 7.2-7.9(8H, m), 10.25(1H, s). |
| 41. | 1.05(6H, d), 1.6(1H, m), 2.05(1H, m), 2.6(1H, m), 3.25(1H, m), 6.1-6.5(3H, m), 7.1-7.75(8H, m), 9.4(1H, s). |
| 42. | 1.65(1H, m), 2.05(1H, m), 2.2(3H, s), 2.65(1H, m), 6.15-6.5(3H, m), 7.1-7.8(7H, m), 9.4(1H, s). |
| 43. | 1.6(1H, m), 2.0(1H, m), 2.6(1H, m), 6.2-6.6(3H, m), 7.1-9.0(7H, m), 9.7(1H, s). |
| 44. | 1.75(1H, m), 2.1(1H, m), 2.15(3H, s), 2.35(3H, s), 2.65(1H, m), 6.2-6.6(3H, m), 7.0-7.8(7H, m), 9.5(1H, s). |
| 45. | 1.65(1H, m), 2.05(1H, m), 2.55(1H, m), 6.1-6.6(3H, m), 7.1-8(8H, m), 10.3(1H, s). |
| 46. | 1.6(1H, m), 2.0(1H, m), 2.2(3H, m), 2.6(1H, m), 6.1-6.6(3H, m), 6.8-7.8(7H, m), 9.3(1H, s). |
| 47. | 1.65(1H, m), 2.05(1H, m), 2.2(3H, s), 2.55(1H, m), 6.1-6.5(3H, m), 7.1-7.7(7H, m), 9.55(1H, s). |

TABLE 4-continued

| Compound No | ¹NMR Data |
|---|---|
| 48 | 1.65(1H, m), 2.06(1H, m), 2.2(3H, s), 2.6(1H, m), 6.15-6.5(3H, m), 6.95.8(7H, m), 9.4(1H, s) |
| 49 | 1.6(1H, m), 2.0(1H, m), 2.55(1H, m), 6.1-6.5(3H, m), 6.8-8.2(13H, m), 9.5(1H, s) |
| 50 | 1.7(1H, m), 2.05(1H, m), 2.55(1H, m), 2.6(6H, s), 6.1-6.6(3H, m), 6.9-8.1(8H, m), 9.15(1H, s) |
| 51 | 1.3(3H, t), 1.65(1H, m), 2.05(1H, m), 2.6(1H, m), 4.3(2H, q), 6.2-6.6(3H, m), 7.1-8.4(8H, m), 10.7(1H, s) |
| 52 | 1.6(1H, m), 2.1(1H, m), 2.6(1H, m), 6.15-6.6(3H, m), 7.8(7H, m), 9.85(1H, s) |
| 53 | 1.7(1H, m), 2.1(1H, m), 2.55(1H, m), 2.6(3H, s), 6.2-6.6(3H, m), 7.2-8.45(8H, m), 11.4(1H, s) |
| 54 | 1.5(1H, m), 1.85(1H, m), 2.35(1H, m), 5.95-6.3(3H, m), 6.9-7.6(7H, m), 9.4(1H, s) |
| 55 | 1.6(1H, m), 1.95(3H, s), 2.1(1H, m), 2.6(1H, m), 4.9(1H, s), 5.2(1H, s), 6.15-6.5(3H, m), 7.1-7.7(8H, m), 9.2(1H, s) |
| 56 | 1.7(1H, m), 2.05(1H, m), 2.6(1H, m), 6.2-6.55(3H, m), 7(1H, dd), 7.2-7.75(6H, m), 7.9(1H, dd), 9.45(1H, s) |
| 57 | 1.65(1H, m), 2.05(2.55(1H, m), 4.5(1H, s), 6.2-6.5(3H, m), 7.05-7.9(8H, m), 9.35(1H) |
| 58 | 1.7(1H, m), 2.1(1H, m), 2.6(1H, m), 6.2-6.6(3H, m), 7.2-8.3(8H, m), 10.0(1H, s), 10.95(1H, s) |
| 59 | 1.65(1H, m), 2.05(1H, m), 2.55(1H, m), 6.2-6.5(3H, m), 7.1-8(8H, m), 9.8(1H) |
| 60 | 1.7(1H, m), 2.1(1H, m), 2.6(1H, m), 3.9(3H, s), 6.15-6.6(3H, m), 7.1-8.4(8H, m), 10.8(1H, s) |
| 61 | 0.9(3H, t), 1.5(2H, m), 1.65(1H, m), 2.05(1h), 2.55(3H, m), 6.1-6.53(3H, m), 7.1-7.75(8H, m), 9.4(1H, s) |
| 62 | 1.7(1H, m), 2.05(1H, m), 2.6(1H, m), 6.2-6.6(3H, m), 7.2-8.2(8H, m), 9.9(1H, s) |
| 63 | 1.55(1H, m), 1.8(1H, m), 2.3(1H, m), 2.4(3H, s), 5.8-6(2H, m), 6.45(1H, d), 7.0-7.7(7H, m), 9.45(1H, d) |
| 64 | 1.65(1H, m), 2.1(1H, m), 2.55(1H, m), 4.5(2H, s), 6.1-6.5(3H, m), 7.1-7.7(8H, m), 9.5(1H, s) |
| 65 | 1.65(1H, m), 2.0(1H, m), 2.55(1H, m), 6.1-6.5(3H, m), 6.8-7.7(8H, m), 9.9(1H, m) |
| 66 | 1.55(1H, m), 1.8(1H, m), 2.35(1H, m), 5.8-6.2(2H, m), 6.5(1H, dd), 7-7.75(8H, m), 8.5(1H, d) |
| 67 | 1.65(1H, m), 2.05(1H, m), 2 and 2.3(3H, s), 2.6(1H, m), 6-6.4(3H, m), 7.1-7.95(7H, m), 9.45(1H, s) |
| 68 | 1.7(1H, m), 2.05(1H, m), 2.2(3H, s), 2.6(1H, m), 6.15-6.55(3H, m), 7-7.7(8H, m), 9.4(1H, s) |
| 69 | 1.7(1H, m), 2.15(1H, m), 2.55(1H, m), 6.15-6.55(3H, m), 7.1-7.85(7H, m), 9.6(1H, s) |
| 70 | 1.8(1H, m), 2.2(1H, m), 2.25(3H, s), 2.65(1H, m), 6.1-6.55(3H, m), 7-7.65(7H, m), 9.4(1H, s) |
| 71 | 1.65(1H, m), 2.05(1H, m), 2.0 and 2.3(3H, s), 2.2(3H, s), 2.6(1H, m), 6-6.4(3H, m), 7.8(7H, m), 9.3(1H, s) |
| 72 | 1.5(1H, m), 1.8(1H, m), 2.25(3H, s), 2.35(1H, m), 5.8-6.1(2H, m), 6.4-6.6(1H, t), 6.95-8(10H, m) |
| 73 | 1.45(1H, m), 1.85(1H, m), 2.0(3H, s), 2.35(1H, m), 6.0-6.3(3H, m), 6.75-7.7(8H, m), 9.2(1H, s) |
| 74 | 1.55(1H, m), 1.85(1H, m), 2.3(3H, s), 2.4(1H, m), 5.8-6.1(2H, m), 6.5(1H, t), 7-7.65(9H, m), 7.95(1H, s) |
| 75 | 1.6(1H, m), 1.9(1H, m), 2.45(1H, m), 5.9-6.15(2H, m), 6.5(1H, dd), 7-7.7(9H), 8.5(1H, d) |
| 76 | 1.6(1H, m), 1.85(1H, m), 2.25(3H, s), 2.35(3H, s), 2.4(1H, m), 5.8-6(2H, m), 6.45(1H, d), 6.9-7.6(8H, m), 7.95(1H, s) |
| 77 | 1.5(1H, m), 1.8(1H, m), 2.25(3H, s), 2.3(1H, m), 2.35(3H, s), 5.75-6(2H, m), 6.4(1H, d), 6.9-7.3(6H, m), 7.65(2H, d), 7.95(1H, s) |
| 78 | 1.7(1H, m), 2.1(1H, m), 2.2(3H, s), 2.6(1H, m), 6.15-6.5(3H, m), 6.8-7.6(7H, m), 9.4(1H, s) |
| 79 | 1.55(1H, m), 2.0(3H, s), 2.05(1H, m), 2.45(1H, m), 5.9-6.3(3H, m), 6.7(1H, td), 7-7.45(5H, m), 9.2(1H, s) |
| 80 | 1.7(1H, m), 2.2(1H, m), 2.65(1H, m), 6.2-6.5(3H, m), 7.15-7.8(6H, m), 9.7(1H, s) |
| 81 | 1.65(1H, m), 2.1(3H, s), 2.2(1H, m), 2.6(1H, m), 6-6.5(3H, m), 6.9-7.1(6H, m), 9.45(1H, s) |
| 82 | 1.6(1H, m), 2.1(1H, m), 2.2(3H, s), 2.55(1H, m), 6.1-6.5(3H, m), 6.9-7.6(7H, m), 9.45(1H, s) |
| 83 | 1.65(1H, m), 2.1(1H, m), 2.6(1H, m), 6.1-6.5(3H, m), 7.15-7.8(7H, m), 9.7(1H, s) |
| 84 | 1.65(1H, m), 2.0(1H, m), 2.2(3H, s), 2.55(1H, m), 6.1-6.5(3H, m), 7.0-7.6(9H, m), 9.4(1H, s) |
| 85 | 1.65(1H, m), 1.95(1H, m), 2.55(1H, m), 6.2-6.5(3H, m), 7.1-7.6(8H, m), 7.8(1H, d), 9.65(1H, s) |
| 86 | 1.6(1H, m), 2.1(1H, m), 2.5(1H, m), 5.4(2H, d), 6.4(3H, m), 7.4(8H, m), 9.7(1H, s) |

TABLE 4-continued

| Compound No. | $^1$NMR Data |
|---|---|
| 87. | 1.4(1H, m), 1.9(1H, m), 2.4(1H, m), 6.1(3H, m), 6.6(3H, m), 7.1(2H, m), 7.6(3H, m), 9.3(1H, s), 9.6(1H, s). |
| 88. | |
| 89. | See experimental |
| 90. | |
| 91. | 1.85(1H, m), 2.05(1H, m), 2.75(1H, m), 6.2–6.6(3H, m). 7.1–7.75(7H, m), 7.8(1H, d), 9.6(1H, s). |
| 92. | 1.85(1H, m), 2.05(1H, m), 2.2(3H, s), 2.8(1H, m). 6.2–6.45(2H, m), 6.55(1H, t), 7–7.7(8H, m), 9.35(1H, s). |
| 93. | 1.85(1H, m), 2.05(1H, m), 2.2(3H, s), 2.3(3H, s), 2.8(1H, m), 6–6.2(2H, m), 6.4(1H, d), 7.0–7.7(7H, m), 9.25(1H, s). |
| 94. | 1.8(1H, m), 2.0 and 2.3(3H, s), 2.05(1H, m), 2.2(3H, s), 2.8(1H, m), 6.0–6.5(3H, m), 7–8.1(7H, m), 9.2 and 9.3(1H, s). |
| 95. | 1.9(1H, m), 2.0 and 2.3(3H, s), 2.05(1H, m), 2.8(1H, m), 6.05–6.5(3H, m), 7.1–8.1(7H, m), 9.4 and 9.45(1H, s). |
| 96. | See experimental |
| 97. | |
| 98. | 1.65(1H, m), 2.05(1H, m), 2.2(3H, s), 2.6(1H, m), 6.2–6.85(3H, m), 7.1–76(7H, m), 9.8(1H, s). |
| 99. | 1.7(1H, m), 2.1(1H, m), 2.6(1H, m), 6.25–6.6(2H, m), 6.8(1H, dd), 7.25–7.6(7H, m), 9.95(1H, s). |
| 100. | 1.7(1H, m), 2.1(1H, m), 2.2(3H, s), 2.6(1H, m), 6.2–6.85(3H, m), 7.1–7.7(7H, m), 9.8(1H, s). |
| 101. | 1.7(1H, m), 2.1(H, m), 2.7(1H, m), 6.2–6.9(3H, m), 7.2–7.7(7H, m), 10.0(1H, s). |
| 101–111 | See experimental |
| 112. | 0.8(3H, d), 1.2(3H, d), 1.4(1H, m), 1.7(1H, m), 2.1(3H, s), 2.1(1H, m), 4.8(1H, m), 5.5(1H, d), 5.8(1H, m), 6.2(1H, m), 6.9–7.6(8H, m). |
| 113. | 0.9(6H, m), 1.3(1H, m), 1.6(1H, m), 1.8(1H, m), 2.1(3H, s), 2.1(1H, m), 3.0(1H, m), 4.0(1H, m), 5.6(1H, d), 5.8(1H, m), 6.2(1H, m), 6.9–7.5(8H, m). |
| 114. | 1.0(6H, d), 1.4(1H, m), 1.7(1H, m), 2.1(1H, m), 5.0(1H, m), 5.5(1H, d), 5.7(1H, m), 6.1(1H, m), 6.9–7.5(9H, m). |
| 115. | 1.4(1H, m), 1.7(1H, m), 2.1(3H, s), 2.1(1H, m), 3.2(3H, s), 5.6(1H, d), 5.8(1H, m), 6.2(1H, m), 6.9–7.5(8H, m). |
| 116. | 1.4(1H m), 1.7(1H, m), 2.1(3H, s), 2.1(1H, m), 2.2(3H, s), 3.1(3H, s), 5.4(1H, s), 5.7(1H, m), 6.0(1H, d), 6.9–7.5(7H, m). |
| 117. | 1.5(1H, m), 1.8(1H, m), 2.0(3H, s), 2.2(1H, m), 4.5(1H, d), 5.3(1H, d), 5.7(1H, d), 5.8(1H, m), 6.3(1H, m), 6.8–7.6(13H, m). |
| 118. | 1.5(1H, m), 1.8(1H, m), 2.2(1H, m), 3.3(3H, s), 5.6(1H, d), 5.8(1H, m), 6.3(1H, m), 6.9–7.6(8H, m). |
| 119. | 1.5(1H, m), 1.7(1H, m), 2.1(1H, m), 2.2(3H, s), 3.2(3H, m), 5.5(1H, s), 5.8(1H, m), 6.1(1H, d), 6.9–7.6(7H, m). |

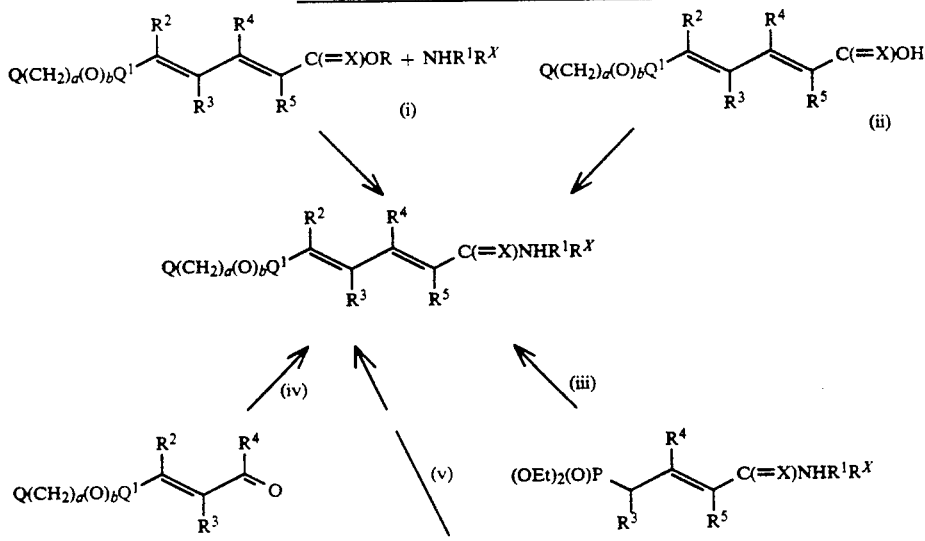

Scheme 1
Preparation of compounds of formula 1.

Scheme 1
Preparation of compounds of formula 1.
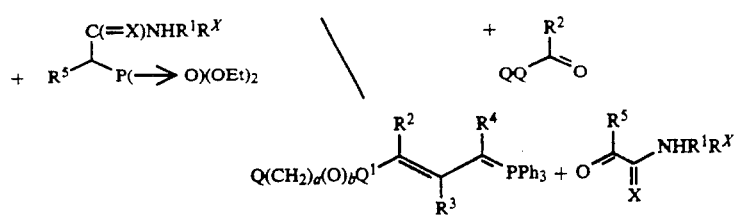
(i) Process (a) $Z^1 = OR$, $X = O$
(ii) Process (a) $Z^1 = OH$, $X = O$
(iii) Process (b) $X = O, S$
(iv) Process (b) $X = O, S$
(v) Process (b) $X = O, S$
Scheme 2
Preparation of ester intermediates
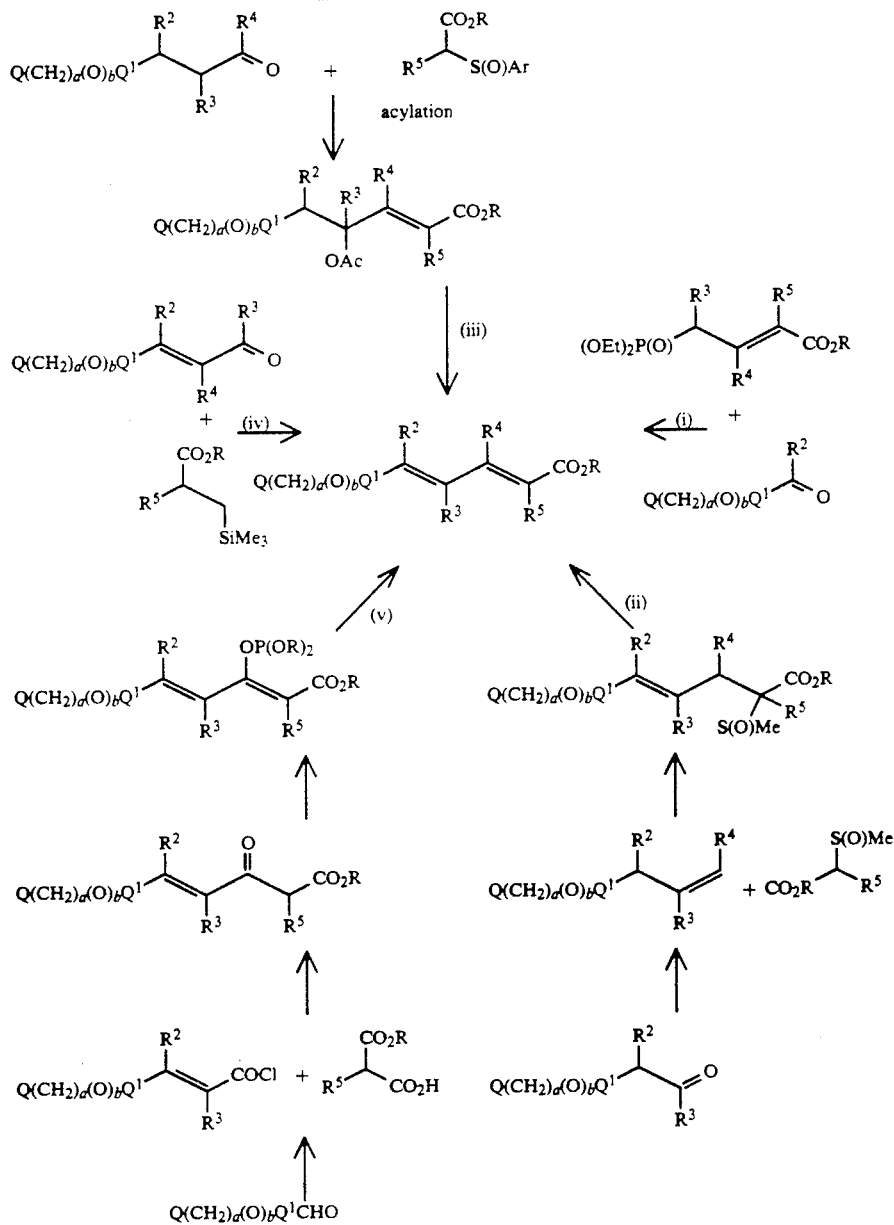

-continued

Scheme 2
Preparation of ester intermediates (i) to (v) denote processes (i) to (v) described hereinbefore for preparation of ester intermediates.

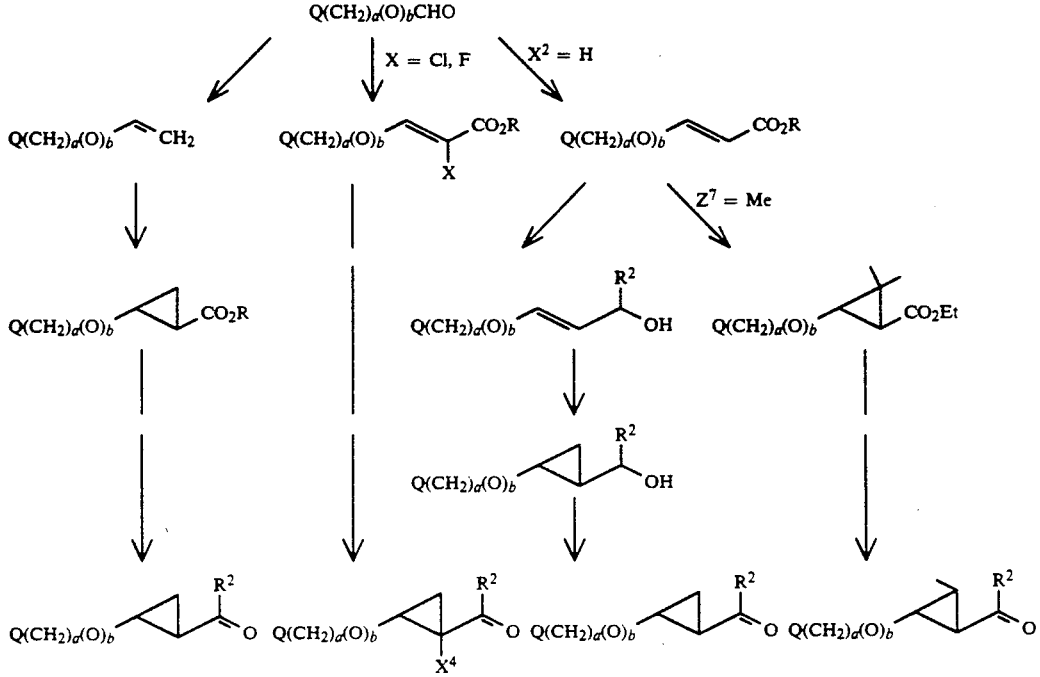

Scheme 3
Preparation of alcohol and aldehyde intermeidiates.

We claim:
1. A compound of the formula (I):

or a salt or propesticide thereof, wherein Q is an aromatic monocyclic or fused bicyclic ring system in which at lest one ring is aromatic;

$Q^1$ is a 1,2-cyclopropyl ring optionally substituted by one or more groups selected from $C_{1-3}$ alkyl, halo, $C_{1-3}$ haloalkyl, $C_{2-3}$ alkynyl, or cyano;

a=0 or 1; b=0 or 1;

$R^2$, $R^3$, $R^4$ and $R^5$ are the same or different with at least one being hydrogen and the other being independently selected from hydrogen, halo, $C_{1-4}$ alkyl or $C_{1-4}$ haloalkyl;

X is oxygen or sulphur;

$R^1$ is phenyl optionally substituted by 1-5 substituents chosen from:
a) $C_{1-4}$ alkyl, $C_{1-4}$ alkoxy, phenoxy each optionally substituted by 1 to 5 halo and methylenedioxy;
b) halo, cyano, nitro, formyl, $C_{1-5}$ acyl;
c) $C_{2-3}$ alkynyl, $C_{2-3}$ alkenyl, each optionally substituted by 1 to 5 halo;
d) a group $S(O)_n R^7$ wherein n=0, 1, 2 and $R^7$ is $C_{1-4}$ alkyl, halo or $NR^{8''}R^{9''}$ wherein $R^{8''}$ and $R^{9''}$ are independently selected from hydrogen, $C_{1-4}$ alkyl and $C_{1-4}$ acyl;
and a group e) $NR^{8''}$ wherein $R^{8''}$ and $R^{9''}$ are as defined above;

$R^x$ is hydrogen or $C_{1-8}$ alkyl or benzyl group; the aromatic ring of Q being optionally substituted with at least one member of the group consisting of hydrocarbyl and alkoxy of 1 to 6 carbon atoms optionally substituted with up to 5 halogens; methylenedioxy, halogen; —CN; —NO$_2$; formyl; acyl of an organic carboxylic acid of up to 5 carbon atoms; alkenyl and alkynyl of 2 to 3 carbon atoms optionally substituted with up to 5 halogens; —S(O)$_n$—$R^7$, n is 0 or 1 or 2 and

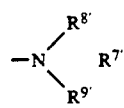

is selected from the group consisting of alkyl of 1 to 4 carbon atoms optionally substituted with at least one halogen, halogen and

$R^{8'}$ and $R^{9'}$ are individually hydrogen or alkyl of 1 to 4 carbon atoms, $R^{8'}$ and $R^{9'}$ are individually hydrogen or alkyl of 1 to 4 carbon atoms; or —COR$^{10}$ and R$^{10}$ is alkyl or alkoxy of 1 to 6 carbon atoms.

2. A propesticide compound of the formula (I) according to claim 1 in which $R^x$ is replaced by $R^{x_1}$, $R^{x_1}$ is selected from:
(A) —Y(D)$_a$=A where A is O or S, Y is phosphorus or carbon, D is hydrogen, $C_{1-4}$ alkyl, $C_{1-4}$ alkoxy, $C_{1-5}$ acyl or aryl or $CO_2D^1$ where $D^1$ is an $C_{1-4}$ alkyl or aryl, and a is 1 or 2

(B) —$S(O)_bD^2$ where b=0, 1 or 2 and $D^2$ is an (i) $C_{1-4}$ alkyl, aryl, aryloxy, or $C_{1-4}$ alkoxy, wherein an aryl ring may be substituted by one or more halo, nitro, cyano, $C_{1-4}$ alkyl, $C_{1-4}$ alkoxy groups each in turn optionally substituted by one or more halogens, or (ii) $D^2$ is a group $ND^3D^4$ wherein $D^3$ is —$COD^5$ where $D^5$ is hydrogen, fluorine or $C_{1-4}$ alkyl; or $D^3$ is $C_{1-4}$ alkyl substituted by $C_{1-5}$ acyl or aryl, carboalkoxy or cyano, or $D^3$ is a group $CO_2D^6$ a where $D^6$ is $C_{1-4}$ alkyl or aryl; D is hydrogen or $C_{1-4}$ alkyl.

3. A compound of the formula (I) according to claim 2 in which $R^x$ is hydrogen or $C_{1-4}$ alkyl or a group (B) —$S(O)_3D^2$ where b is o and $D^2$ is phenyl; or a group (A)

where A is O, and D is hydrogen or $C_{1-4}$ alkoxy and a is 1 or 2.

4. A compound of the formula (I) according to claim 1 in which $Q^1$ is a 1,2-cyclopropyl ring and b=0 and a=0.

5. A compound of the formula (I) according to claim 1 in which the 3- position of the cyclopropyl ring $Q^1$ is unsubstituted and the 1- and 2- positions are unsubstituted or substituted by fluoro or chloro.

6. A compound of the formula (I) according to claim I in which $R^1$ is phenyl optionally substituted by 1 to 3 groups selected from alkyl, $C_{1-4}$ alkyl substituted by 1-5 halo, halo, $C_{1-4}$ alkoxy optionally substituted by 1-5 halo.

7. A compound of the formula (II):

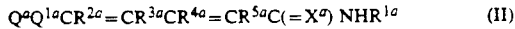

or a salt thereof, wherein $Q^a$ is an optionally substituted phenyl or pyridyl group or an optionally substituted fused bicyclic ring system of which at least one ring is aromatic and containing 0 or 1 nitrogen atoms or 0 or 1 sulphur atoms.

$Q^{1a}$ is a 1,2-disubstituted cyclopropyl ring optionally substituted by one or more groups selected from $C_{1-3}$ alkyl, halo, or $C_{1-3}$ haloalkyl; $R^{2a}$, $R^{3a}$, $R^{4a}$ and $R^{5a}$ are the same or different with at least one being hydrogen and the others being independently selected from hydrogen, halo, $C_{1-4}$ alkyl or $C_{1-4}$ haloalkyl; $X^a$ is oxygen or sulphur; $R^{1a}$ is selected from phenyl optionally substituted by halo and optionally substituted $C_{1-4}$ alkyl.

8. A compound selected from:

(±)-(2E,4E)-N-Phenyl-5-[c-2-(3,4-dibromophenyl)-r-1-fluorocyclopropyl]-3-methylpenta-2,4-dienamide (±)-(2E,4E)-N-(2-Chlorophenyl)-5-[c-2-(3,4-dibromophenyl)-r-1-fluorocyclopropyl]penta-2,4-dienamide (±)-(2E/Z,4E)-N-(2-Methylphenyl)-5-fc-2-(3,4-dibromophenyl)-r-1-fluorocyclopropyl]-3-methyl-penta-2,4-dienamide (2E:2Z=3:1)

(±)-(2E,4E)-N-(2-Methylphenyl)-5-[c-2-(3,4-dibromophenyl-r-1-fluorocyclopropyl]-3-methylpenta-2,4-dienamide (±)-(2E,4E)-N-(2-Bromophenyl)-5-[c-2-(3,4-dibromophenyl)-r-1-fluorocyclopropyl]penta-2,4-dienamide (±)-(2E,4E)-N-(2-Methylphenyl)-5-[c-2-(3,4-dibromophenyl)-r-1-fluorocyclopropyl]penta-2,4-dienamide (±)-(2E,4E)-N-(4-Fluoro-2-methylphenyl)-5-[c-2-(3,4-dibromophenyl)-r-1-fluorocyclopropyl]penta-2,4-dienamide (±)-(2E,4E)-N-(5-Fluoro-2-methylphenyl)-5-[c-2-(3,4-dibromophenyl)-r-1-fluorocyclopropyl]penta-2,4-dienamide (±)-(2E,4E)-N-(2,4-Difluorophenyl)-5-[c-2-(3,4-dibromophenyl)-r-1-fluorocyclopropyl]penta-2,4-dienamide (±)-(2E,4E)-N-(2-Chlorophenyl)-5-[c-2-(3,4-dibromophenyl)-r-1-fluorocyclopropyl]-3-methyl-penta-2,4-dienamide (±)-(2E,4E)-N-(2-Methylphenyl)-5-[c-2-(3,4-dichlorophenyl)-r-1-fluorocyclopropyl]penta-2,4-dienamide (±)-(2E,4E)-N-(2-Methylphenyl)-5-[r-1-fluoro-c-2-(3,4,5-trichlorophenyl)cyclopropyl]penta-2,4-dienamide (±)-(2E/Z,4E)-N-(2-Methylphenyl)-5-[c-2-(3,4-dichlorophenyl)-r-1-fluorocyclopropyl]-3-methyl-penta-2,4-dien- amide (2E:2Z=1:1)

(±)-(2E,4E)-N-(2-Methylphenyl)-5-[c-2-(3-chloro-4-iodophenyl)-r-1-fluorocyclopropyl]penta-2,4-dienamide (±)-(2E,4E)-N-(2-Methylphenyl)-5-[r-1-fluoro-c-2-(4-trifluoromethylphenyl)cyclopropyl]-3-methylpenta-2,4-dienamide (±)-(2E,4E)-N-(2-Methylphenyl)-5-[r-1-fluoro-c-(4-iodophenyl)cyclopropyl]-3-methylpenta-2,4-dienamide (±)-(2E,4E)-N-(5-Fluoro-2-methylphenyl)-5-[c-2-(3,4-dichlorophenyl)-r-1-fluorocyclopropyl]penta-2,4-dienamide (±)-(2E,4E)-N-(4-Fluoro-2-methylphenyl)-5-[r-1-fluoro-c-2-(3,4,5-trichlorophenyl)cyclopropyl]penta-2,4-dienamide (±)-(2E,4E)-N-(4-Fluoro-2-methylphenyl)-5-[c-2-(3,4-dichlorophenyl)-r-1-fluorocyclopropyl]penta-2,4-dienamide (±)-(2E,4E)-N-(2-Methylphenyl)-5-[c-2-(4-bromophenyl)-r-1-fluorocyclopropyl]penta-2,4-dienamide (±)-(2E,4E)-N-(2-fluoromethylphenyl)-5-[c-2-(3,4-dibromophenyl)-r-1-fluorocyclopropyl]penta-2,4-dienamide (−)-(2E,4E)-N-(2-Methylphenyl)-5-[(1R, 2S)-2-(3,4-dibromophenyl)-1-fluorocyclopropyl]penta-2,4-dienamide (±)-(2E,4E)-N-(2-Methylphenyl)-5-[r-1-chloro-c-(3,4-dichlorophenyl)-cyclopropyl]-3-methylpenta-2,4-dienamide (±)-(2E,4E)-N-(2-Methylphenyl)-5-[r-1-chloro-c-2-(3,4-dibromophenyl)cyclopropyl]penta-2,4-dienamide (±)-(2E,4E)-N-(2-Methylphenyl)-5-[r-1-chloro-c-2-(3,4-dibromophenyl)cyclopropyl)-3-methylpenta-2,4-dienamide (±)-(2Z,4E)-N-(2-Methylphenyl)-5-[c-2-(3,4-dibromophenyl)-r-1-fluorocyclopropyl]-2-fluoro-3-methyl-penta-2,4-dienamide (±)(2Z,4E)-N-(2-Chlorophenyl)-5-[c-2-(3,4-dibromophenyl)-r-1-fluorocyclopropyl]-2-fluoro-3-methyl-penta-2,4-dienamide (±)-(2Z,4E)-N-(2-Methylphenyl)-5-[c-2-(3,4-dichlorophenyl)-r-1-fluorocyclopropyl]-2-fluoropenta-2,4-dienamide (±)-(2Z,4E)-N-(2-Methylphenyl)-5-[c-2-(3,4-dibromophenyl)-r-1-fluorocyclopropyl]-2-fluoropenta-2,4-dienamide (−)-(2E,4E)-N-(2-Methylphenyl)-5-[(1R,2S)-trans-2-(3,4-dibromophenyl)cyclopropyl]-3-methylpenta-2,4-dienamide (±)-(2E,4E)-N-Methyl-N-phenyl-5-[c-2-(3,4-dibromophenyl)-r-1-fluorocyclopropyl]penta-2,4-dienamide (±)-(2E,4E)-N-(2-Chlorophenyl)-N-methyl-5-[c-2-(3,4-dibromophenyl)-r-1-fluorocyclopropyl]penta-2,4,dienamide (±)-(2E,4E)-N-(2-Chlorophenyl)-N-methyl-5-[c-2-(3,4-dibromophenyl)-r-1-fluorocyclopropyl]-3-methylpenta-2,4-dienamide (±)-(2E,4E)-N-(2-Methylphenyl)-N-carboethoxy-5-[c-2-(3,4-dibromophenyl)-r-1-fluorocyclopropyl]-penta-2,4-dienamide.

9. An pesticidal composition comprising a compound of formula (I) as defined in claim 1 in admixture with a carrier or diluent.

10. A synergised pesticidal composition comprising a compound of formula (I), as defined in claim 1, a synergist for the formula I compound and a carrier or diluent.

11. A mixture of a compound of formula (I) as defined in claim 1 and another pesticidal compound.

12. A method for the control of pests comprising application to the pest or to an environment susceptible to pest infestation of a pesticidally effective amount of a compound according to claim 1.

13. A method according to claim 12 wherein the environment is an animal.

14. A method according to claim 12 wherein the environment is a plant or tree.

15. A method according to claim 12 wherein the environment is stored products.

* * * * *